United States Patent
Dorisio Deininger et al.

(10) Patent No.: US 7,918,977 B2
(45) Date of Patent: Apr. 5, 2011

(54) SOLID STATE ELECTROCHEMICAL GAS SENSOR AND METHOD FOR FABRICATING SAME

(75) Inventors: Debra J. Dorisio Deininger, Longmont, CO (US); Clayton J. Kostelecky, Longmont, CO (US)

(73) Assignee: Synkera Technologies, Inc., Longmont, CO (US)

( * ) Notice: Subject to any disclaimer, the term of this patent is extended or adjusted under 35 U.S.C. 154(b) by 945 days.

(21) Appl. No.: 11/533,729

(22) Filed: Sep. 20, 2006

(65) Prior Publication Data

US 2007/0102294 A1 May 10, 2007

Related U.S. Application Data

(60) Provisional application No. 60/597,070, filed on Nov. 8, 2005.

(51) Int. Cl.
*G01N 27/26* (2006.01)
*G01N 27/407* (2006.01)

(52) U.S. Cl. ........ 204/424; 204/431; 429/304; 205/784; 205/781; 205/786.5; 205/787; 205/779.5

(58) Field of Classification Search .................. 204/412, 204/411, 410, 421–429, 431, 432; 429/304; 205/781, 784, 786.5, 787, 779.5
See application file for complete search history.

(56) References Cited

U.S. PATENT DOCUMENTS

| | | | |
|---|---|---|---|
| 4,025,412 A | 5/1977 | LaConti | 204/195 R |
| 4,172,022 A | 10/1979 | Lidorenko et al. | 204/195 S |
| 4,728,588 A | 3/1988 | Noding et al. | 429/127 |
| 4,925,544 A | 5/1990 | Goldring | 204/421 |
| 4,948,490 A | 8/1990 | Venkatasetty | 204/412 |
| 5,001,023 A | 3/1991 | Cheshire et al. | |
| 5,173,166 A * | 12/1992 | Tomantschger et al. | 204/412 |
| 5,215,643 A | 6/1993 | Kusanagi et al. | 204/412 |
| 5,227,043 A | 7/1993 | Shakushiro et al. | 204/421 |
| 5,302,274 A | 4/1994 | Tomantschger et al. | 204/412 |
| 5,510,209 A | 4/1996 | Abraham et al. | 429/192 |
| 5,527,446 A | 6/1996 | Kosek et al. | 205/792.5 |
| 5,548,474 A | 8/1996 | Chen et al. | 361/313 |
| 5,716,506 A | 2/1998 | Maclay et al. | 204/424 |

(Continued)

FOREIGN PATENT DOCUMENTS

WO    WO 96/29711    9/1996

OTHER PUBLICATIONS

Chu et al. (Novel composite polymer electrolyte comprising mesoporous structured SiO2 and PEO/Li, Solid State Ionics, 156, 2003, pp. 141-153).*

Appatecci et al. (Hot-pressed, dry, composite, PEO-based electrolyte membranes, Journal of Power Sources, 114, 2003, 105-112).*

(Continued)

*Primary Examiner* — Alexa D Neckel
*Assistant Examiner* — Jennifer Dieterle
(74) *Attorney, Agent, or Firm* — Marsh Fischmann & Breyfogle LLP

(57) ABSTRACT

An electrochemical gas sensor, a method for making the sensor and methods for the detection of a gaseous species. The electrochemical gas sensor is a solid-state gas sensor that includes a solid polymer electrolyte. A working electrode is separated from a counter electrode by the solid polymer electrolyte. The sensor can include a multilaminate structure for improved detection properties, where electrode microbands are disposed within the solid polymer electrolyte.

54 Claims, 12 Drawing Sheets

U.S. PATENT DOCUMENTS

| | | | |
|---|---|---|---|
| 5,739,193 A | 4/1998 | Walpita et al. | 524/413 |
| 5,749,927 A | 5/1998 | Chern et al. | 29/623.5 |
| 6,190,805 B1 | 2/2001 | Takeuchi et al. | |
| 6,337,009 B1 | 1/2002 | Nadanami et al. | 205/775 |
| 6,454,923 B1 | 9/2002 | Dodgson et al. | 204/415 |
| 6,513,362 B1 | 2/2003 | Yadav et al. | 73/31.05 |
| 6,613,207 B1 | 9/2003 | De La Prieta et al. | 204/426 |
| 6,652,723 B1 | 11/2003 | Nadanami et al. | 204/424 |
| 6,695,958 B1 | 2/2004 | Adam et al. | 204/403.01 |
| 6,752,964 B1 | 6/2004 | Grubbs et al. | 422/98 |
| 6,824,661 B2* | 11/2004 | Lawless | 204/426 |
| 2002/0046947 A1* | 4/2002 | Lawless | 204/426 |
| 2003/0024814 A1* | 2/2003 | Stetter | 204/426 |
| 2009/0078917 A1* | 3/2009 | Percec et al. | 252/583 |

OTHER PUBLICATIONS

Morales et al. (Electrochimica Acta 45, 1999, 1049-1056).*
International Search Report and Written Opinion issued Sep. 11, 2007 for PCT Application No. PCT/US06/60623.
D'Epifanio et al., "Metallic-Lithium, $LiFePO_4$- based Polymer Battery Using Peo-$ZrO_2$ Nanocomposite Polymer Electrolyte"; Journal of Applied Electrochemistry 34; 403-408, 2004.
Park et al.; "Electrochemical Stability and Conductivity Enhancement of Composite Polymer Electrolytes"; Solid State Ionics 159; 111-119 (2003).
Xi et al.; "Enhanced Electrochemical Properties of PEO-based Composite Polymer Electrolyte With Shape-Selective Molecular Sieves", Journal of Power Sources; (Jul. 25, 2005).

* cited by examiner

Typical Sensor Response to 10 ppm H2S

Average Linearity of Sensor Response

SOLID STATE ELECTROCHEMICAL GAS SENSOR AND METHOD FOR FABRICATING SAME

CROSS-REFERENCE TO RELATED APPLICATIONS

This application claims priority to U.S. Provisional Patent Application Ser. No. 60/597,070 filed on Nov. 8, 2005, which is incorporated herein by reference in its entirety.

STATEMENT REGARDING FEDERALLY FUNDED RESEARCH

This invention was funded by the Department of Health and Human Services, through the Centers for Disease Control and Prevention under Grant No. 5R44-OH007471-04, as administrated by the Small Business Innovation Research program. The government has certain rights in this invention.

BACKGROUND OF THE INVENTION

1. Field of the Invention

The present invention relates to solid-state gas sensors for the detection of a chemical species. More particularly, the present invention relates to solid-state electrochemical gas sensors for detecting contaminant gas species and methods for fabricating electrochemical gas sensors.

2. Description of Related Art

Sensors for the detection of chemical species are utilized in myriad applications. For example, the detection of noxious gaseous species such as carbon monoxide (CO), hydrogen sulfide ($H_2S$), volatile organic carbons (VOCs) or nitrogen oxides ($NO_x$) is desirable so that a signal can be generated indicating the presence of such species. Appropriate steps can then be taken to mitigate their effect or to remove persons from the presence of the gaseous species.

Electrochemical sensors for the detection of gaseous species typically utilize large electrodes and liquid electrolytes. Acid electrolytes such as sulfuric acid are the most common liquid electrolytes, although other inorganic and organic liquids have also been utilized. However, sensors based on liquid electrolytes are known to leak under certain operating conditions and are affected by long exposures to very high or very low humidity levels. Sensors utilizing liquid electrolytes must be adequately sealed to prevent leakage of the liquid electrolyte, yet also permit the gaseous species to reach the working electrode/electrolyte interface. This requires a costly and complex sensor design and the effective lifetime of the sensors is still typically limited.

As used herein, an electrochemical sensor is a sensor in which the chemical constituent of interest (i.e., the analyte) is contacted with a catalytic electrode so that the chemical constituent is either oxidized or reduced with the exchange of electrons. The flow of electrical current due to the oxidation and reduction of the chemical constituent is used as a measure of the concentration of the constituent being detected.

One type of electrochemical gas sensor, which is sometimes referred to as an amperometric gas sensor, typically includes three electrodes in contact with an electrolyte. A working electrode is typically fabricated from platinum (Pt) or gold (Au). The gaseous species diffuses to the point where the working electrode and the electrolyte are in contact, where an electrochemical oxidation or reduction reaction occurs resulting in the capture or release of electrons. A counter electrode is used to maintain a charge balance in the sensor and the charge difference (i.e., the current flow) between the working electrode and the counter electrode generates an output signal in the form of an electric current that is proportional to the concentration of the gaseous species. In addition, a reference electrode can be used to control the operation of the sensor by maintaining a selected potential relative to the working electrode. Two electrode configurations are also utilized, where a single electrode functions as both a counter electrode and a reference electrode.

Solid electrolytes have also been utilized for electrochemical sensors. For example, ceramic electrolytes such as yttria stabilized zirconia (YSZ) are known, but require an operating temperature in excess of about 300° C., thereby requiring an on-board heater and substantial power input which render the devices unsuitable for many applications. An example of this type of sensor is disclosed in U.S. Pat. No. 6,613,207 by De La Prieta et al.

Another approach for solid electrolytes is the use of a proton conductive material such as a sulfonated tetrafluoroethylene copolymer, for example NAFION™ (E.I. duPont deNemours, Wilmington, Del.). An example of this type of sensor is disclosed in U.S. Pat. No. 5,215,643 by Kusanagi et al. However, these electrolyte materials require a constant humidity environment to retain adequate conductivity and therefore are not well suited for use in low or very high humidity environments.

U.S. Pat. No. 4,925,544 by Goldring discloses a sensor that includes an electrolyte separated from the analyte by a selectively permeable membrane, where the electrolyte is an electrically conductive solid including a homogeneous dispersion of a polymeric matrix phase and an electrically conductive salt. The polymer matrix is substantially free of water to avoid variability in the sensor due to evaporation of water during use. The polymeric matrix phase can be plasticized, the plasticizer forming a continuous phase in which the conductive salt is dissolved. The sensor is particularly useful for the measurement of blood gases.

U.S. Pat. No. 6,202,471 by Yadav et al. discloses a multi-laminate sensor that includes multiple sensing layers and electrodes in a laminated stack. The sensing layers are fabricated from a material having a material property that changes when exposed to the chemical species of interest, and the material property change is measured by the electrodes.

There remains a need for an electrochemical gas sensor that is capable of operating over a range of moderate temperatures. There is also a need for an electrochemical gas sensor that is capable of operating over a wide range of humidity conditions such that the sensor can adequately function in arid environments as well as in humid environments. There is also a need for an electrochemical gas sensor having a small size and that does not require heat input or other large power input for operation.

SUMMARY OF THE INVENTION

Accordingly, the present invention provides an electrochemical sensor and a method for fabricating the electrochemical sensor. The electrochemical sensor can be utilized for the detection of a chemical species, preferably a gaseous chemical species that can be reduced or oxidized at relatively low potentials. Among the chemical species that can be detected are carbon monoxide (CO), ammonia ($NH_3$), hydrogen sulfide ($H_2S$), hydrocarbons ($C_xH_y$) including volatile organic compounds (VOC's) and ethanol, chlorine ($Cl_2$), chlorine dioxide ($ClO_2$), $NO_x$ compounds such as $NO_2$, and $SO_x$ compounds such as $SO_2$.

The sensor according to the present invention is an electrochemical sensor wherein a reaction of a chemical species is catalyzed at a working electrode. The reaction at the working electrode results in the release of electrons to an external circuit, producing an electrical current that is proportional to the concentration of the chemical species. Ions are conducted through an electrolyte to a counter electrode.

According to one embodiment, an electrochemical sensor is provided. The sensor includes a solid polymer electrolyte that includes a solid polymer matrix and a salt dispersed within the solid polymer matrix. A working electrode is in contact with the solid polymer electrolyte and a counter electrode is in contact with the solid polymer electrolyte, where the working electrode is separated from the counter electrode by the solid polymer electrolyte, which is disposed between the electrodes.

The solid polymer matrix can be selected from the group consisting of poly(oxides), poly(vinyl ethers), polyvinyl pyrrolidone, poly(acrylics), poly(methacrylics) and poly(vinyl alcohol). A particularly useful polymer is a poly(oxide), such as poly(ethylene oxide). The solid polymer matrix is preferably substantially amorphous (non-crystalline), so that the polymer electrolyte maintains good ionic conductivity. The solid polymer matrix can have a molecular weight of at least about 100,000 and not greater than about 10,000,000.

The salt that is dispersed within the solid polymer matrix causes the polymer electrolyte to have good ionic conductivity. Preferably, the salt is a monovalent cation salt. The salt can be an inorganic salt such as one selected from the group consisting of a lithium salt, a sodium salt, an ammonium salt and a magnesium salt. The salt can preferably be selected from the group consisting of lithium perchlorate, lithium tetrafluoroborate, lithium chloride, sodium chlorate, sodium perchlorate, sodium tetrafluoroborate, ammonium tetrafluoroborate and ammonium perchlorate. A particularly useful salt is lithium perchlorate.

The solid polymer electrolyte preferably includes at least about 2 wt. % of the salt and includes not greater than about 25 wt. % of the salt, such as at least about 10 wt. % and not greater than about 15 wt. % of the salt. The solid polymer electrolyte can also include inorganic particulates dispersed within the solid polymer matrix, such as from about 3 wt. % to not greater than about 15 wt. % of the inorganic particulates. The inorganic particulates can include metal oxide particulates such as aluminum oxide, silica and titania and can have an average particle size of not greater than about 1 micrometer, such as from about 5 nanometers to about 500 nanometers.

The working electrode of the sensor is adapted to catalyze the oxidation or reduction of the chemical species of interest. In this regard, the working electrode can include a material selected from the group consisting of gold, platinum, silver, palladium, ruthenium, iridium, carbon and mixtures thereof. In one embodiment, the working electrode includes a noble metal, such as gold or platinum. The working electrode and counter electrode can include the same material or the working electrode can include a material that is different than the counter electrode. In one embodiment, the counter electrode includes platinum metal. The counter electrode can also be a reference electrode, such as in a two-electrode sensor design.

According to one embodiment, the electrochemical sensor is a multi-laminate sensor. The multi-laminate sensor includes a plurality of electrode microbands disposed within the solid polymer electrolyte. For example, the working electrode can include a plurality of planar, spaced-apart microbands that are disposed within the solid polymer electrolyte. The counter electrode can include a plurality of spaced-apart microbands that are also disposed within the solid polymer electrolyte, where the counter electrode microbands are disposed between the working electrode microbands to define layers of solid polymer electrolyte between the microbands. The layers of solid polymer electrolyte disposed between adjacent microbands can have an average thickness of at least about 25 μm and not greater than about 2.5 mm, preferably not greater than about 1 mm. For example, the electrochemical sensor can include at least 5 working electrode microbands and at least 4 counter electrode microbands disposed within the solid polymer electrolyte.

The present invention also provides a method for making an electrochemical sensor. The method can include the steps of mixing at least a polymer, an inorganic salt and a solvent to form a polymer electrolyte mixture and forming the polymer electrolyte mixture into a layer. The mixture is dried to remove solvent therefrom and form a first polymer electrolyte layer having mutually opposed first and second major surfaces. A first working electrode layer is applied to at least a portion of the first major surface and a first counter electrode layer is applied to at least a portion of the second major surface.

To fabricate a multi-laminate sensor having electrode microbands disposed within the polymer electrolyte, the step of applying a first counter electrode layer can include forming a second polymer electrolyte layer having mutually opposed first and second major surfaces. A counter electrode is applied to the first major surface of the second polymer electrolyte layer, and the first major surface of the second polymer electrolyte layer is laminated to the second major surface of the first polymer electrolyte layer such that the first counter electrode layer is disposed between the first and second polymer electrolyte layers, forming an electrode microband. A second working electrode layer can be applied to the second major surface of the second polymer electrolyte layer.

To fabricate additional layers, a third polymer electrolyte layer having mutually opposed first and second major surfaces can be provided and a second working electrode layer can be applied to the first major surface of the third polymer electrolyte layer. Thereafter, the first major surface of the third polymer electrolyte layer can be laminated to the second major surface of the second polymer electrolyte layer such that the second working electrode layer is disposed between the second polymer electrolyte layer and the third polymer electrolyte layer.

The laminating step can include heating to a temperature of not greater than about 70° C. In one embodiment, the polymer electrolyte mixture includes at least about 10 wt. % and not greater than about 30 wt. % of the polymer, at least about 1 wt. % and not greater than about 10 wt. % of the inorganic salt, and at least about 60 wt. % and not greater than about 80 wt. % of the solvent. The solvent can be selected from water, an alcohol or toluene. The step of applying the first working electrode can include applying a particulate material selected from the group consisting of platinum, gold, silver, palladium, ruthenium, iridium, carbon and mixtures thereof. The particulate material can be dispersed within a thick-film paste, and the thick-film paste can also include from about 0.1 wt. % to about 2 wt. % of a polymer electrolyte.

The present invention is also directed to the detection of a chemical species by reacting the chemical species at a working electrode of the sensor and detecting the current created thereby. For example, the chemical species can be $H_2S$, CO or ethanol ($C_2H_6O$).

DESCRIPTION OF THE INVENTION

The present invention will now be described with reference to the attached figures.

Figure 1:
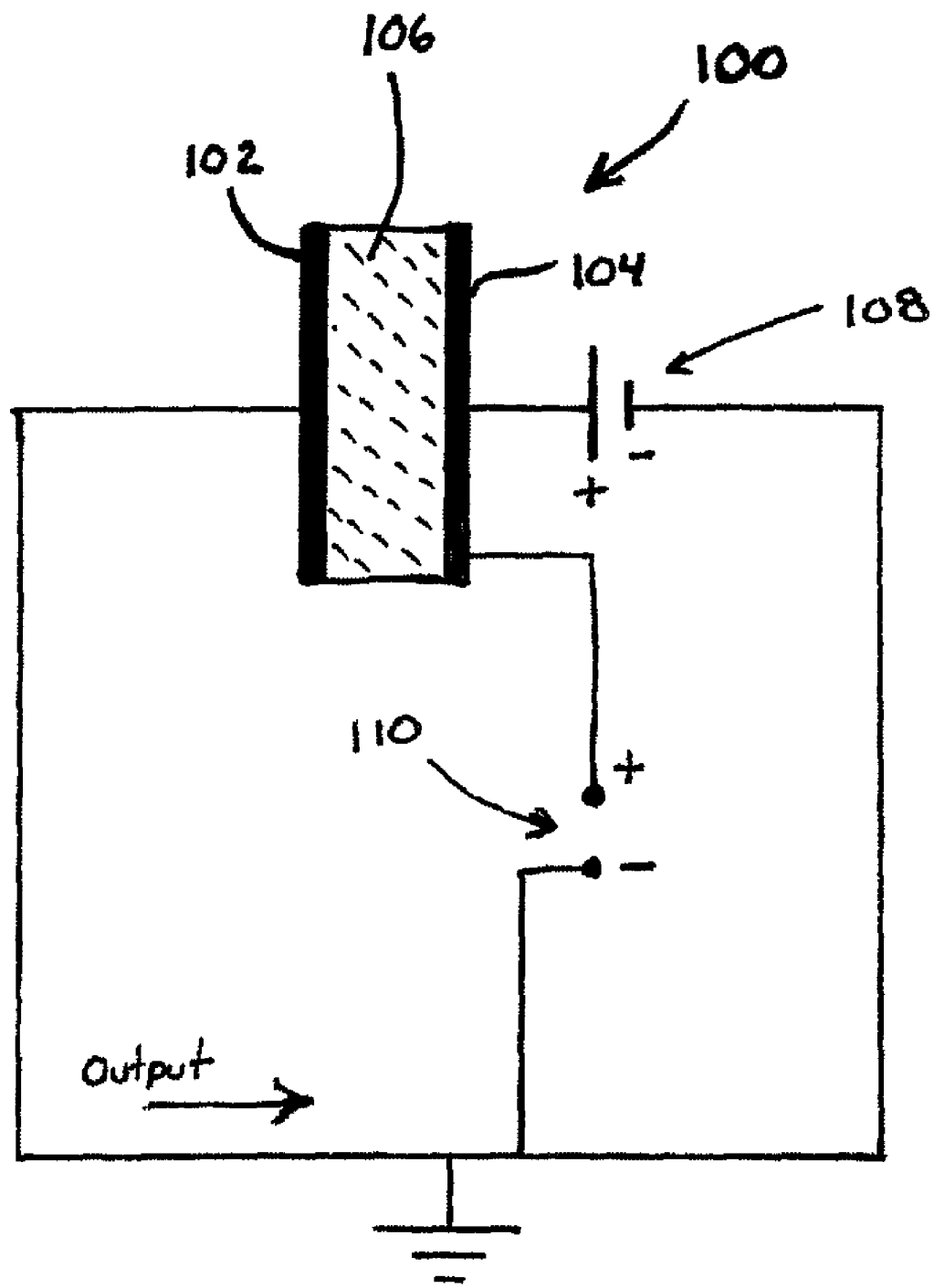
FIG. 1 illustrates an electrochemical gas sensor according to an embodiment of the present invention.

FIG. 1 illustrates an electrochemical sensor 100 for the detection of chemical species and its associated electronic circuitry. The electrochemical sensor 100 illustrated in FIG. 1 is a two-electrode sensor that includes a working electrode 102 that is in contact with a polymer electrolyte 106, and a counter electrode 104 that is also in contact with the polymer electrolyte 106. The counter electrode 104 is spaced apart from the working electrode 102 and is separated therefrom by the polymer electrolyte 106. The counter electrode 104 also functions as a reference electrode in the two-electrode sensor design.

In operation, the interface of the working electrode 102 and the electrolyte 106 is in contact with the environment that is being sampled such that the chemical species of interest (i.e., the analyte) contacts the interface. The working electrode 102 includes a material that is adapted to catalyze the reduction or oxidation of the chemical species being detected. For example, for the detection of $H_2S$, the overall oxidation reaction at the working electrode 102 can be written as:

$$H_2S + 4H_2O \rightarrow H_2SO_4 + 8H^+ + 8e^- \qquad (1)$$

The protons ($H^+$) are transported by ionic conduction through the polymer electrolyte 106 to the reference/counter electrode 102 and the electrons are routed via an output circuit where the potential can be measured across the circuit 110. This potential between the working electrode 102 and the counter electrode 104 provides a measure of the concentration of the chemical species in the vicinity of the working electrode 102. A cell 108 can be used to control the potential of the working electrode 102 with respect to the counter electrode 104 by applying a bias potential.

According to the present invention, the electrochemical sensor includes an ionically conductive electrolyte that is a solid polymer electrolyte, particularly one that includes a salt dispersed within a polymer matrix.

According to the present invention, the polymer that is utilized in the solid polymer electrolyte preferably is chemically and physically stable over a wide range of temperatures. Further, it is preferred that the polymer maintain a substantially amorphous (i.e., non-crystalline) structure over a wide range of temperatures. According to one embodiment, the polymer can maintain an amorphous structure at temperatures as low as −20° C., more preferably as low as −40° C. and even more preferably as low as −60° C. Such low temperatures may be encountered during use of the sensor in cold environments. Further, the polymer preferably maintains an amorphous structure at temperatures of at least about 50° C., more preferably at least about 80° C. and even more preferably at least about 100° C. Such elevated temperatures may be encountered during fabrication or operation of the sensor or a device including the sensor. Polymers having a crystalline structure will have a reduced ionic conductivity, and therefore may not be suitable for many applications requiring high sensitivity.

Examples of useful polymers according to the present invention include poly(oxides), poly(vinyl ethers), polyvinylpyrrolidone, poly(acrylics) and poly(methacrylics). Examples of poly(acrylics) and poly(methacrylics) include, but are not limited to, poly(acrylic acid), poly(ethyl acrylate), poly(3-ethoxyethylacrylate), poly(4-cyanophenyl acrylate), poly(2-cyanoethyl acrylate), poly(4-methoxyphenyl acrylate) and poly(n-pentyl acrylate). In addition, poly(vinyl alcohol) can also be useful. Among these, poly(oxides) are particularly preferred, and in a particularly preferred embodiment the polymer is poly(ethylene oxide). Poly(ethylene oxide) is particularly preferred as it can retain an amorphous structure over a wide range of temperatures.

As is discussed in further detail below, the polymer utilized in the solid polymer electrolyte should be sufficiently workable (e.g., castable) such that the polymer can be fabricated into thin layers having a substantially uniform thickness. In this regard, the molecular weight of the polymer is preferably at least about 100,000 and more preferably at least about 1,000,000. Further, the molecular weight of the polymer is preferably not greater than about 10,000,000 and more preferably is not greater than about 8,000,000. Low molecular weight polymers can result in a polymer electrolyte solution having a very low viscosity that is difficult to process into a uniform layer. Likewise, high molecular weight polymers can be difficult to process into a thin layer due to their high viscosity.

According to the present invention, the solid polymer electrolyte includes a salt dispersed within the solid polymer to provide sufficient ionic conductivity to the electrolyte. The salt can be monovalent salt or a multivalent salt (e.g., a divalent salt) and monovalent salts are particularly preferred due to the relatively small size of the ion. The salt should be selected to be stable in the presence of the solid polymer electrolyte and any absorbed water in the polymer at the potentials used by the sensor. In general, inorganic salts having smaller cations and anions are preferred, such as those anions and cations having an ionic radius of not greater than about 0.1 nm, and cation salts are particularly preferred. Examples of preferred salts include lithium (Li) salts, sodium (Na) salts, ammonium ($NH_4$) salts and magnesium (Mg) salts.

Examples of useful sodium salts include, but are not limited to, sodium chlorate ($NaClO_3$), sodium perchlorate ($NaClO_4$) and sodium tetrafluorborate ($NaBF_4$). Examples of useful ammonium salts include, but are not limited to, ammonium perchlorate ($NH_4ClO_4$) and ammonium tetrafluoroborate ($NH_4BF_4$).

Lithium salts are particularly preferred due to the small ionic radius of the $Li^+$ ion and examples of useful lithium salts include, but are not limited to, lithium perchlorate ($LiClO_4$) and lithium tetrafluorborate ($LiBF_4$). It has been found that lithium perchlorate in particular forms a polymer electrolyte mixture having very good processing properties for fabricating the electrochemical sensors of the present invention.

In addition to the foregoing, other salts of lithium, sodium, ammonium or magnesium can be useful, such as triflate salts (e.g., lithium trifluoromethanesulfonate), hexafluorophosphate salts (e.g., lithium hexafluorophosphate) or bistrifluoromethanesulfonamide salts (e.g., lithium bistrifluoromethanesulfonamide).

The solid polymer electrolyte preferably includes enough of the salt to impart sufficient ionic conductivity to the polymer electrolyte so that ions can be efficiently transported from the working electrode to the counter electrode. Accordingly, it is preferred that the solid polymer electrolyte comprise at least about 2 wt. % of the salt. In order to provide good ionic conductivity, the solid polymer electrolyte more preferably includes at least about 5 wt. % of the salt and even more preferably at least about 10 wt. % of the salt. However, too high a concentration of the salt can result in the solid polymer electrolyte being difficult to process into a thin and uniform layer, and therefore the solid polymer electrolyte preferably includes not greater than about 25 wt. % of the salt and even more preferably not greater than about 15 wt. % of the salt.

According to one preferred embodiment, the solid polymer electrolyte further includes particulates dispersed within the polymer, such as inert, inorganic particulates. The presence of a small amount of inorganic particulates can advantageously prevent crystallization of the polymer, and therefore the polymer electrolyte can maintain sufficient ionic conductivity over a wider range of temperatures. It has also been found that the presence of inorganic particulates can improve the processing properties (e.g., castability) of the polymer electrolyte layers during fabrication of the sensor. According to one embodiment, the solid polymer electrolyte preferably comprises at least about 3 wt. % inorganic particulates and preferably not greater than about 15 wt. % of the inorganic particulates. Preferably, the inorganic particulates are ceramic particulates, such as metal oxide particulates. Such particulates can include, for example, aluminum oxide, silica and titania. To inhibit crystallization and maintain workability of the polymer electrolyte, the inorganic particulates are preferably nanoparticles having an average particle size of not greater than about 1 μm. According to one embodiment, the inorganic particles preferably have an average particle size of at least about 5 nanometers and not greater than about 500 nanometers.

The sensor according to the present invention includes a working (sensing) electrode. The working electrode is adapted to catalyze the oxidation or reduction of the analyte at the interface of the working electrode, the electrolyte and the analyte, known as the three-phase interface. In a two-electrode design (e.g., FIG. 1), the sensor includes a reference/counter electrode that is separated from the working electrode by the electrolyte such that a potential across the working electrode and the reference/counter electrode is created and can be measured. In a three-electrode sensor design, the sensor includes a separate counter electrode and reference electrode.

The working electrode can include materials that are adapted to catalyze the oxidation or reduction reaction of the chemical species of interest. Such materials can be selected from, for example, gold (Au), platinum (Pt), silver (Ag), palladium (Pd), carbon (e.g., carbon nanotubes), ruthenium (Ru) and iridium (Ir), as well as mixtures of such elemental materials and compounds, such as silver/silver chloride (Ag/AgCl). Noble metals are particularly useful and gold and platinum are preferred for many applications. The working electrode materials are preferably in particulate form such that the working electrode has a high surface area to promote the oxidation or reduction of the analyte. In this regard, the working electrode is preferably fabricated by depositing particulate materials on the polymer electrolyte, as is discussed below.

The counter electrode and reference electrode can include similar materials. For some applications, the working electrode, counter electrode and reference electrode can be fabricated from the same material(s), whereas for other applications the electrodes, particularly the microbands in a multilaminate sensor will preferably include different materials.

The working electrode and/or the counter electrode can also include the polymer electrolyte dispersed within the electrode, such as between the active electrode material. This can enhance the performance of the sensor by increasing the amount of 3-phase contact (electrode/electrolyte/analyte). The polymer also can increase the adhesion of the electrodes to the polymer electrolyte. For example, the polymer electrolyte can be dissolved into the solvent (vehicle) of an electrode paste that is used to fabricate the electrode, as is discussed below.

According to a preferred embodiment of the present invention, the sensor is a multilaminate sensor, where at least one of the working electrode and the counter electrode includes spaced-apart microbands disposed within the polymer electrolyte, such that a thin layer of electrolyte separates adjacent electrode microbands. Such a structure can advantageously increase the sensitivity of the sensor, while maintaining a relatively small size.

When fabricated from the sensor materials of the present invention, a multilaminate sensor can advantageously provide increased temporal resolution (i.e., fast response), an ability to utilize electrolytes have a relatively low ionic conductivity and can also generate a higher signal to noise ratio (SNR) due to an increase in faradaic currents relative to non-faradaic currents.

Figure 2:
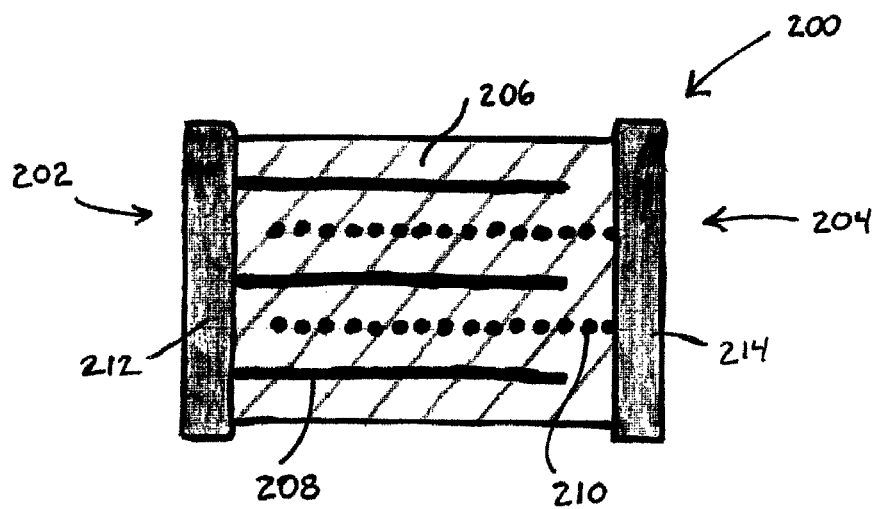
FIG. 2 illustrates a cross-section of an electrochemical gas sensor according to another embodiment of the present invention.

A multilaminate sensor according to the present invention is illustrated in FIG. 2. The multilaminate sensor 200 includes a working electrode 202 and a counter/reference electrode 204, which are separated by a solid polymer electrolyte 206.

The working electrode 202 includes a plurality of planar, spaced-apart electrode microbands 208 that are disposed within the electrolyte 206 and a termination portion 212. The microbands 208 of the working electrode 202 are electrically connected by the termination portion 212 of the working electrode that is disposed on the exterior of the sensor 200. The termination portion 212 also provides electrical contact with the associated electronic circuitry. The counter/reference electrode 204 includes a plurality of spaced-apart electrode microbands 210 that are also disposed within the electrolyte 206 and that are disposed between adjacent working electrode microbands 208 so that the distance between the working electrode microbands 208 and an adjacent counter/reference electrode microband 210 is relatively small. The counter/reference electrode 204 also includes a termination portion 214 electrically connecting the microbands 210 providing electrical contact with associated electronic circuitry.

The microband portions of the electrodes are preferably fabricated using the electrode materials discussed above, such as gold or platinum. However, the termination portions 212 and 214 can be fabricated from a different electronically conductive material, and preferably are fabricated from a high conductivity material such as silver.

The microbands 208 and 210 preferably have a thickness that is at least about 0.2 μm and preferably is not greater than about 5 μm. As is illustrated in FIG. 2, at least one counter/reference electrode microband 210 is disposed between two working electrode microbands 208 with layers of electrolyte 206 disposed therebetween. It is generally preferred that the layers of polymer electrolyte between adjacent microbands be as thin as reasonably possible, and preferably the layers have an average thickness of not greater than about 2.5 mm, and more preferably not greater than about 1 mm. However, the layers should not be so thin that the layers are susceptible to defects such as pinholes within the electrolyte layer, and therefore the layers preferably have an average thickness of at least about 25 μm.

A portion of the interface between the working electrode 202 and the electrolyte 206 is in contact with the environment surrounding the sensor 200, such that the chemical species of interest can contact the interface and react at the interface of the working electrode microbands 208 and the electrolyte 206. Thus, the outer edges of the working electrode microbands 208 preferably extend to the exterior surface of the sensor. The counter/reference electrode microbands 210 can optionally be buried within the electrolyte to minimize the exposure of the microbands 210 to the environment. This is more clearly illustrated in the exploded schematic view illustrated in FIG. 3.

Figure 3:
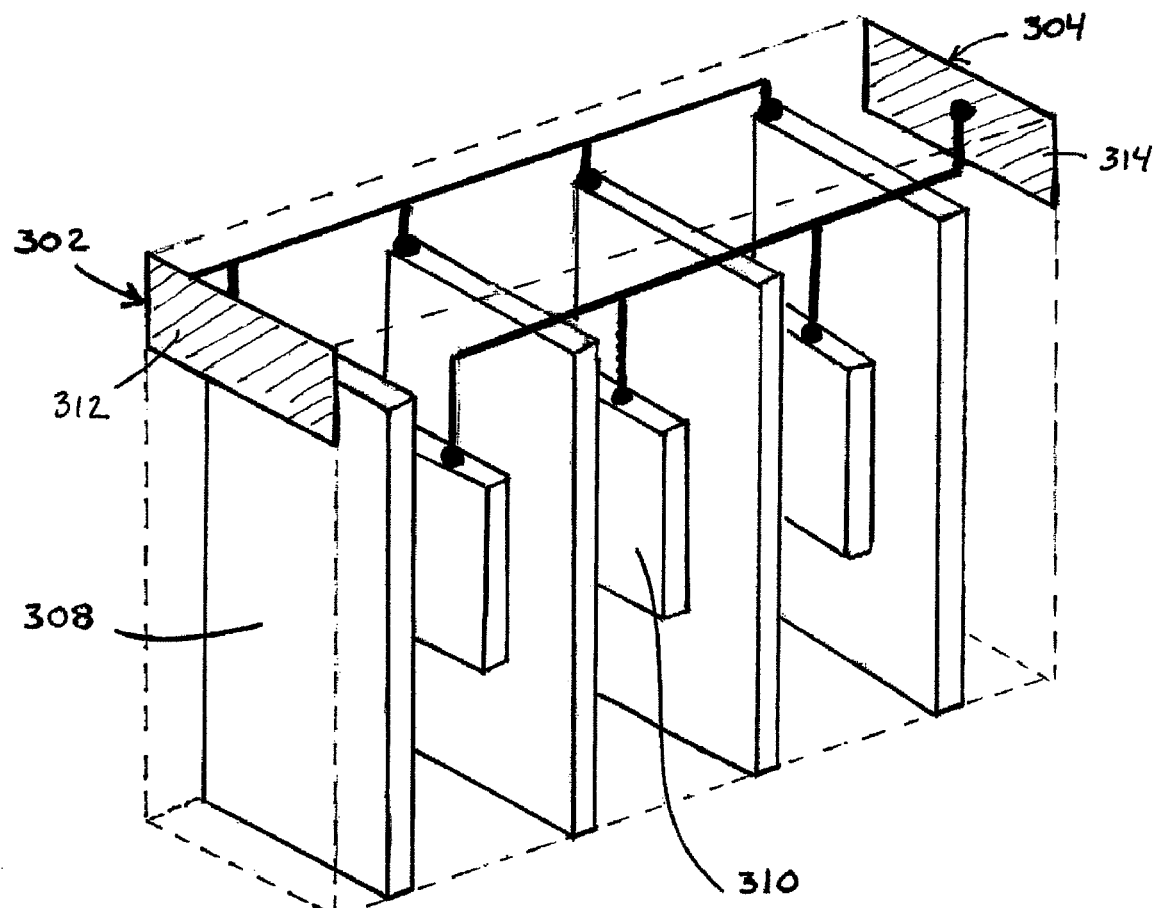
FIG. 3 illustrates a schematic view of an electrochemical gas sensor according to an embodiment of the present invention.

The exploded schematic view illustrated in FIG. 3 illustrates the electrode structure of the sensor and for purposes of clarity the electrolyte is not illustrated. The microbands 308 of the working electrode 302 are exposed to the external environment at the edges of the sensor so that the analyte can contact the working electrode 302 at the point where the electrode contacts the electrolyte. Thus, most of the desired reaction(s) occur at the exposed edges of the microbands 308. However, since the polymer electrolyte is not completely dense, some analyte may diffuse into the electrolyte and react on the internal surfaces of the microbands 308.

In contrast, the microbands 310 of the counter/reference electrode 304 are buried within the electrolyte. That is, the microbands 310 are not directly exposed to the environment, such as at the edges of the sensor. This is preferred when the working electrode microbands 308 and the counter/reference electrode microbands are fabricated using the same electrode material (e.g., platinum). However, the counter/reference electrode microbands can often be exposed without significantly hindering sensor operation. Each of the electrodes 302 and 304 include termination portions 312 and 314 that are electrically connected to the microbands and provide a means for electrical communication with the circuitry associated with the sensor.

Figure 4:
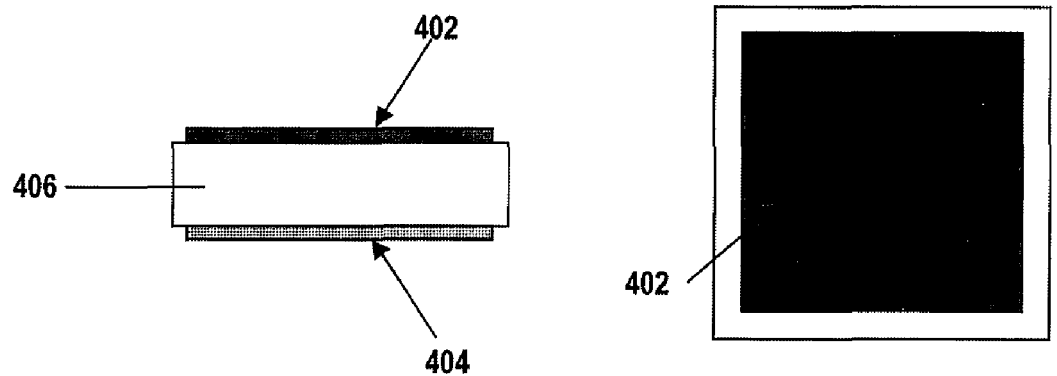
FIG. 4 illustrates the structure of an electrochemical gas sensor according to an embodiment of the present invention.

The physical structure of the sensor according to the present invention can include a variety of forms, some of which are illustrated in FIGS. 4-8. FIG. 4 illustrates one sensor design, similar to that illustrated in FIG. 1, that includes a single working electrode 402 and a single counter/reference electrode 404, where the electrodes are separated by a layer of solid polymer electrolyte 406. This sensor can be particularly useful in low-cost applications that do not require a high degree of sensitivity.

Figure 5:
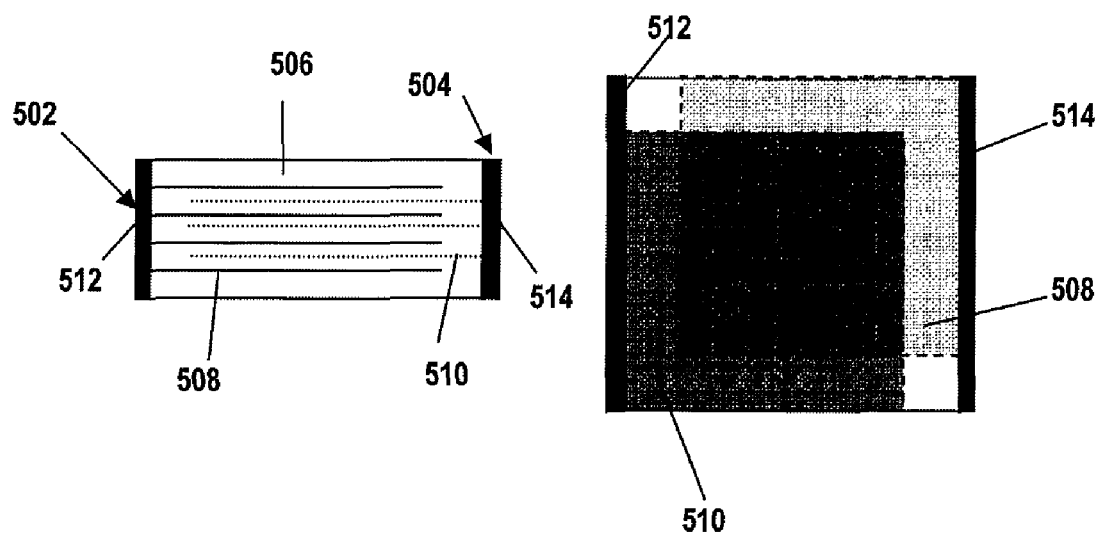
FIG. 5 illustrates the structure of an electrochemical gas sensor according to an embodiment of the present invention.

FIG. 5 illustrates a multilaminate sensor similar to that illustrated in FIG. 2 where each of the working electrode 502 and the counter/reference electrode 504 includes microbands disposed within the polymer electrolyte 506. The working electrode 502 includes microbands 508 that are spaced apart and are disposed in substantially parallel relation. The counter/reference electrode 504 also includes a plurality of microbands 510 that are disposed between the microbands 508 of the working electrode 502. In an alternative embodiment, the counter/reference electrode microbands 510 can be disposed between every other working electrode microband 508, such that two working electrode microbands 508 are disposed between adjacent counter/reference electrode microbands 510. In this embodiment, the planar surface of the working electrodes and the counter/reference electrodes are slightly offset as illustrated by the top view of the sensor.

Figure 6:
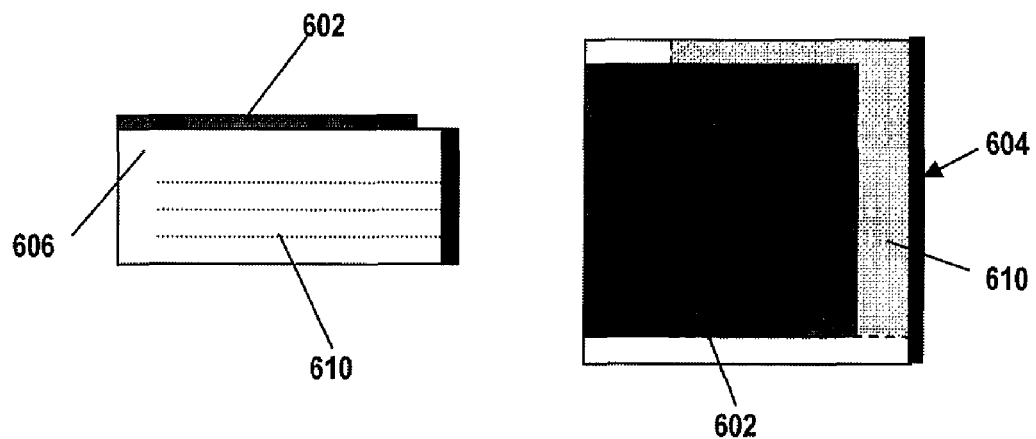
FIG. 6 illustrates the structure of an electrochemical gas sensor according to an embodiment of the present invention.

FIG. 6 illustrates an alternative embodiment that includes a counter/reference electrode 604 having microbands 610 disposed within the electrolyte 606. A working electrode 602 is disposed on a surface of the solid polymer electrolyte 606 and at least a portion of the working electrode 602 overlaps a plane defined by the counter/reference electrode microbands 610.

Figure 7:
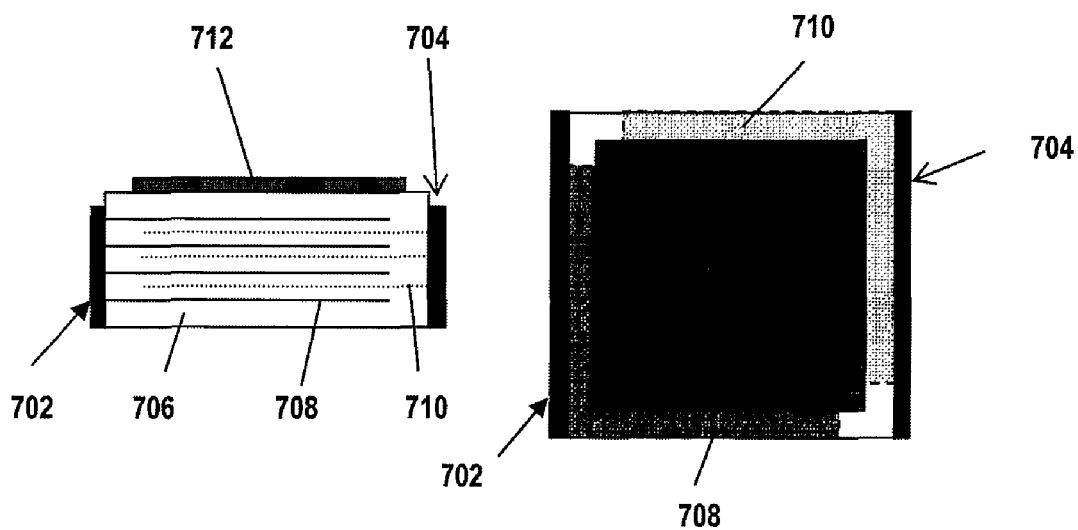
FIG. 7 illustrates the structure of an electrochemical gas sensor according to an embodiment of the present invention.

The sensor according to the present invention can also comprise three electrodes, including a separate and distinct counter electrode and reference electrode. A sensor according to this embodiment is illustrated in FIG. 7. In a two-electrode sensor where a single electrode acts as both the counter electrode and the reference electrode, only the potential between the two electrodes is known and the potential drop between the working electrode and the electrolyte is not precisely known. A three electrode sensor includes a separate reference electrode that takes up a potential that is predetermined based upon the calculated redox potential of the chemical species of interest. With the potential of the working electrode controlled with respect to the reference electrode, three electrode sensors are more stable than two electrode sensors since the potential across the working electrode/electrolyte interface can be varied independently of the counter electrode.

Referring to FIG. 7, the sensor includes a working electrode 702 having microbands 708 disposed within a polymer electrolyte 706. A counter electrode 704 includes microbands 710 also disposed within the polymer electrolyte 706 that are disposed between the working electrode microbands 708. A reference electrode 712 is disposed on top of the sensor. Associated electronic circuitry (not illustrated) can be used to apply a potential between the working electrode 702 and the reference electrode 712.

Figure 8:
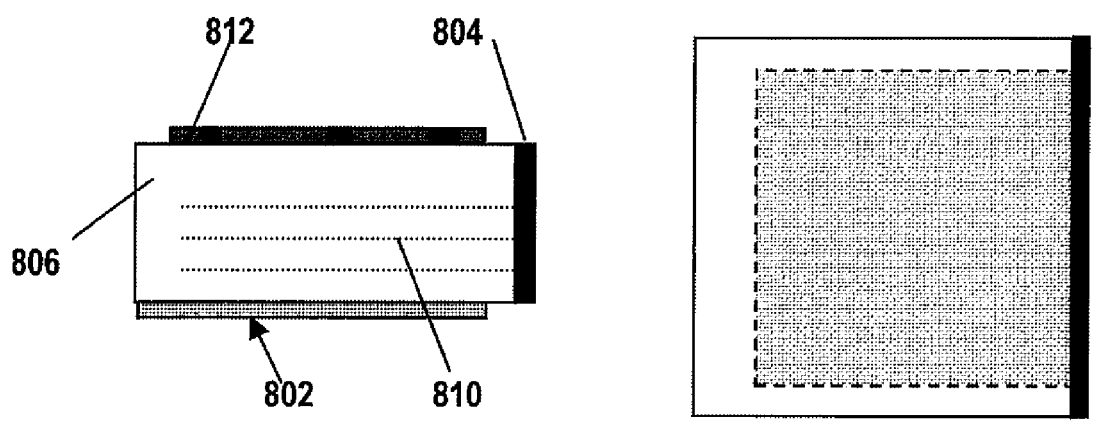
FIG. 8 illustrates the structure of an electrochemical gas sensor according to an embodiment of the present invention.

FIG. 8 illustrates an alternative embodiment where both the reference electrode 812 and the working electrode 802 are disposed on opposed surfaces of the solid polymer electrolyte

806. The counter electrode includes microbands 810 disposed within the polymer electrolyte 806.

The present invention also relates to a method for fabricating an electrochemical sensor. In one embodiment, the present invention relates to a method for fabricating a multi-laminate sensor, as is described above. The fabrication process involves the production of polymer electrolyte layers and internal electrode microbands within the polymer electrolyte. The layers can be built up to form a multi-layer pad, which can then be diced (cut) to form individual, chip-style sensor devices.

In a first step of the method, a multi-layer structure that includes a polymer electrolyte layer and an electrode layer is provided. One method for providing such a structure is to form a polymer electrolyte mixture into a thin layer, such as by casting, and then dry the mixture to form a solid polymer electrolyte layer having opposed major surfaces. Thereafter, an electrode layer can be applied to a surface of the electrolyte layer. This process can be repeated multiple times to form a number of sheets that can be stacked and laminated to form a multilayer structure having alternating layers of electrode material and polymer electrolyte.

A similar method can also be used to fabricate a two-electrode sensor such as that illustrated in FIG. 4, that is, one without electrode microbands disposed within the polymer electrolyte. In this method, a polymer electrolyte mixture is formed into a layer and the layer is then dried. A working electrode and a counter electrode are then applied to opposite surfaces of the polymer electrolyte to form the sensor. To increase the thickness of the polymer electrolyte, multiple polymer electrolyte layers can be stacked and laminated before applying the electrodes to the outer surfaces of the electrolyte.

Figure 9:
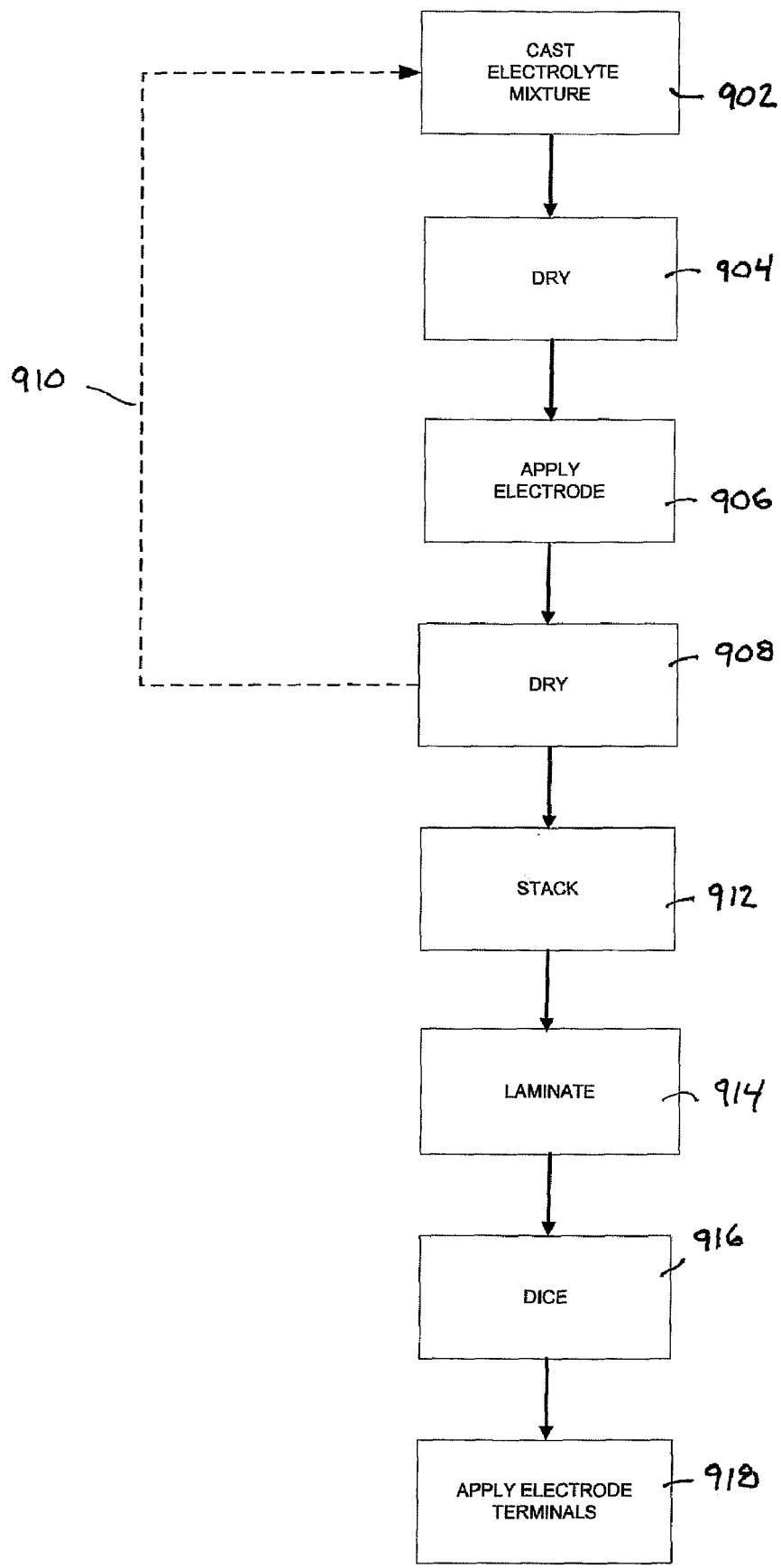
FIG. 9 is a flow chart illustrating a method for producing an electrochemical gas sensor according to an embodiment of the present invention.

One particular embodiment of the method of the present invention will now be described with reference to FIG. 9, which is a flowsheet illustrating a method for the production of a multilaminate sensor.

A fluid (e.g., flowable) polymer electrolyte mixture is formed by providing a polymer or polymer precursor and also providing a salt for dispersion within the polymer. The polymer and the salt are mixed in a solvent, such as water, or an organic solvent such as an alcohol (e.g., methanol), toluene, or mixtures thereof. Mixtures of two or more solvents can be useful to ensure adequate dissolution of both the polymer and the salt. The solvent can also be selected to have a vapor pressure that enables rapid drying time of the mixture. Preferably, the castable polymer electrolyte mixture will include at least about 1 wt. % and not greater than about 10 wt. % of the inorganic salt, at least about 10 wt. % and not greater than about 30 wt. % of the polymer and at least about 60 wt. % and not greater than about 80 wt. % of the solvent(s).

In addition, as is discussed above, particulates can be included in the polymer electrolyte composition to enhance the properties of the polymer electrolyte layer. These particulates can be added directly to the polymer electrolyte mixture or a precursor to the particulates can be added to the mixture that will result in the particulates being formed in-situ during subsequent processing of the polymer electrolyte layer. An example of such a precursor is one formed by a sol-gel method from, for example, tetraethylorthosilicate (TEOS) or tetraethylorthotitanate (TEOT). When the particulates are added to the mixture, it is preferred that the mixture include at least about 2 wt. % and not greater than about 20 wt. % of the particulates.

The polymer electrolyte mixture is then formed into a thin layer. The thin layer can be formed by casting the mixture 902 onto a flat surface, such as by tape casting or a similar technique. For example, the polymer electrolyte composition can be formed into a thin layer by spin coating, dip coating, tape casting, hand casting, screen printing or a similar method. In one embodiment, the polymer electrolyte is cast onto an inert sheet such as MYLAR, a biaxially oriented polyester film available from E.I. duPont deNemours, Wilmington, Del., USA. The sheet can be coated with a release material, such as silicone, to promote release of the cast layer from the sheet after drying. The as-cast (wet) layer of the polymer electrolyte mixture preferably has a thickness of at least about 15 mils (about 0.35 mm) and preferably not greater than about 25 mils (about 0.65 mm).

Thereafter, the polymer electrolyte mixture is dried 904 to remove solvent from the polymer electrolyte mixture and form a polymer electrolyte layer. The drying step can be performed at room temperature or can be assisted, such as by the use of heated lamps or similar devices to accelerate the drying process. The drying step forms a dried polymer electrolyte layer having mutually opposed first and second major surfaces. The removal of solvent results in the layer shrinking, and in one embodiment the dried polymer electrolyte layer has an average thickness of at least about 10 mils (about 0.25 mm) and preferably not greater than about 50 mils (about 1.27 mm).

The dried polymer electrolyte layer can optionally be pressed at this stage to decrease the possibility of pinholes in the layer and to further consolidate the layer. Further, the polymer electrolyte layer can be cut or trimmed into sheets of a desired size for subsequent processing.

An electrode material is then applied 906 to at least one of the major surfaces of the dried polymer electrolyte layer. The electrode can be applied using a variety of methods such as a physical sputtering, physical vapor deposition, chemical vapor deposition, ion beam or e-beam deposition and the like. Preferably, the electrode material is applied using a thick-film deposition process, where an electrode pattern is formed in a screen and a thick-film electrode composition is selectively screen printed onto the polymer electrolyte layer. Thick film deposition and similar techniques that enable the deposition of particulate materials (e.g., particulate metals) are preferred so that the electrode materials can have a high surface area. Preferably, the thick-film electrode paste composition includes the primary electrode material, such as platinum or gold, and also includes some of the polymer electrolyte to improve adhesion and to improve the three phase interface of the electrode material. In one embodiment, the thick film paste includes at least about 0.1 wt. % and not greater than about 2 wt. % of the polymer electrolyte material and more preferably includes at least about 0.5 wt. % of the polymer material. The thick-film paste also includes solvents and other liquid carriers to permit the application of the paste through the screen. The thick-film paste is formulated to dry at the low temperatures used to fabricate the sensor, such as not greater than about 100° C. and more preferably not greater than about 80° C. After deposition of the paste 906, the paste is allowed to dry 908 to form the electrode layer.

To form a two-electrode sensor according to the present invention that does not include microbands (e.g., FIG. 4), a second electrode material can be applied to the second (opposite) major surface of the polymer electrolyte layer. The second electrode material can be applied in a manner similar to the first electrode material, and the second electrode material can be the same or different than the first electrode material.

To form a multilaminate electrochemical sensor according to the present invention, the foregoing process is repeated 910 to form a second polymer electrolyte layer also having mutually opposed first and second major surfaces. To form the laminated stack, a counter electrode material is applied to the first major surface of the second polymer electrolyte layer. The second polymer electrolyte layer is then stacked 912 onto the first polymer electrolyte layer and can be lightly pressed to adhere to the first polymer electrolyte layer. Thus, the counter electrode material contacts the second major surface of the first polymer electrolyte layer, opposite the working electrode. This process can be repeated multiple times to form a stack of alternating polymer electrolyte and electrode materials, such as the electrochemical sensor illustrated in FIG. 5.

Thereafter, the stack can be laminated 914 by pressing and heating such that the polymer flows slightly to form a monolithic structure. For example, the structure can be isostatically pressed, such as at a pressure of from about 100 psi to about 4000 psi (about 0.7 MPa to about 27.6 MPa) and a temperature of from about 30° C. to about 80° C., preferably not greater than about 70° C. The lamination step 914 can advantageously remove any air pockets and further consolidates the structure.

Thereafter, the laminated structure can be diced 916 to form individual multi-laminate structures. The termination portions of the electrodes can then be applied 918, such as by applying a conductor paste composition, such as a silver paste or copper paste, to the edges of the individual multi-laminate structures.

The electrochemical sensor of the present invention can be utilized in a number of devices and in a variety of applications. For example, the sensor can be worn by a person to alert the person of dangerous levels of toxic gas species in the air. The sensor can also be used for monitoring gas concentrations in industrial processes, such as combustion processes. As is known to those skilled in the art, the sensor can be placed behind a membrane, diffusion restrictor or similar device to control the amount of chemical species from the surrounding environment that comes in contact with the sensor. The membrane or diffusion restrictor can also be used to restrict the amount of potentially interfering contaminants that reach the sensor.

Figure 10:
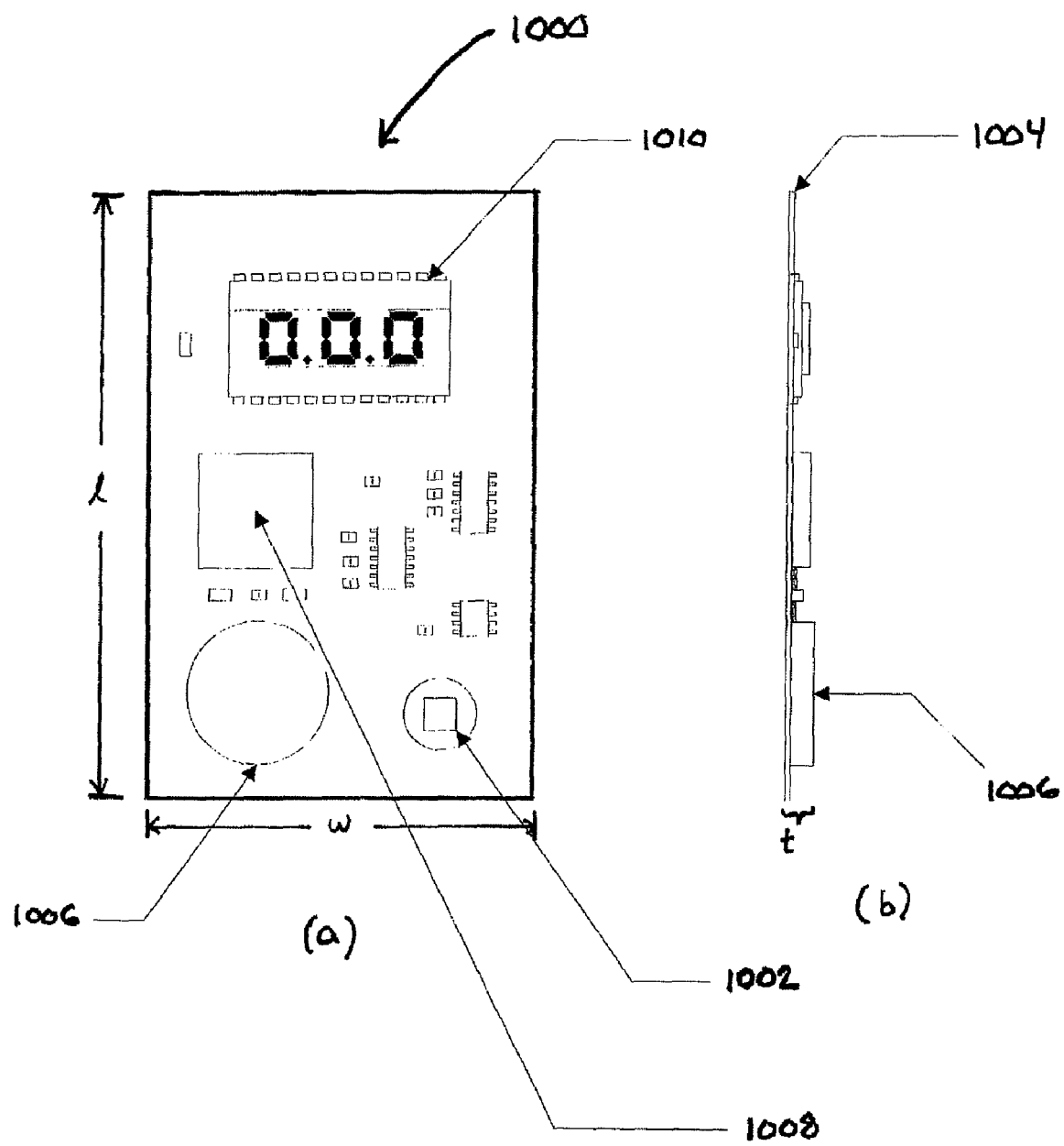
FIGS. 10(a) and (b) illustrate a device including an electrochemical gas sensor component according to the present invention.

One device utilizing the sensor according to the present invention is illustrated in FIG. 10. The device 1000 is a smart card that includes an electrochemical sensor 1002 attached to a circuit board 1004, such as by using a conductive adhesive. The board can be a printed circuit board (PCB), such as one having a thickness of 1/32 inch. The board 1004 could also be a flexible circuit board. A battery 1006 is provided to power the sensor and other associated electronics. The associated electronics connect the sensor 1002 to a sounder 1008, which is capable of providing an audible signal to a person wearing the smart card 1000. In addition, a digital display 1010 can be provided to indicate the concentration of the chemical species of interest in the environment, such as in ppm. The associated electronics can include, by way of example, a signal processor, such as an A/D converter, to process the signal from the sensor 1002. The device 1000 can also be provided with other components in addition to or in lieu of those illustrated in FIG. 10. For example, the device could include a visible alarm such as a red LED and/or a vibratory alarm. An indicator of battery life can also be included, as well as a self-test mechanism to permit testing of the device.

The device illustrated in FIG. 10 advantageously can have a small size to enable a user to easily attach the device to an article of clothing so that it can be comfortably worn. For example, the smart card device 1000 can have a length (l) of not greater than 100 mm and a width (w) of not greater than about 60 mm, with a maximum thickness (t) of not greater than about 4 mm. The device can also be light weight and can have a mass of not greater than about 30 g. The small size of the electrochemical sensor 1002 according to the present invention advantageously enables the construction of such a small and lightweight device, and permits the sensor 1002 to be mounted onto the surface of the device, such as by using a conductive adhesive, eliminating the need for more costly interconnections.

During operation, a bias potential can be applied across the sensor. Typically, the bias potential will be in the range of about −1 volt to about +1 volt, such about −200 millivolts to about +200 millivolts, particularly for a platinum/air reference electrode. The selected bias voltage can depend upon the gaseous chemical species being detected and the reference electrode materials being used. The bias potential should be sufficient to oxidize or reduce the chemical species of interest, however a potential that is too high will tend to oxidize the electrodes.

The electrochemical sensor according to the present invention can be utilized to detect a wide range of chemical species for a variety of purposes. For example, the electrochemical sensor can be used for the detection of $H_2S$. The sensor can also be used for the detection of CO in industrial, commercial and residential spaces, VOC's in ambient air and in breath (ethanol), and ammonia ($NH_3$), such as in refrigeration applications, chemical processing applications such as quality control, petroleum refining, explosives manufacturing, agriculture and stack gas emissions.

The sensor according to the present invention can provide numerous advantages. The sensor can have a substantially linear output, which increases the accuracy of a device incorporating the sensor. The response time can be very rapid, particularly with the use of interdigitated microband electrodes. The sensor can also have very low detection limits. For example, the sensor can detect levels of a contaminant gas species such as $H_2S$ in quantities of 50 ppb (parts per billion) to 100's of ppm. The sensor structure is leak-free, can have a small size, is physically robust and can be fabricated in large quantities at a relatively low cost. The sensor can consume very low levels of power, enabling a small battery to be used. The sensor can operate over a range of temperatures that are commonly encountered in a working environment and does not require, for example, an on-board heater to raise the temperature of the electrolyte. The sensor can also operate over a wide range of humidity conditions without a substantial degradation in performance. The sensor can also have a long operating lifetime.

EXAMPLES

The present invention can be understood with reference to the following examples.

For each of the following examples, a sensor is generally prepared as follows.

A polymer and a salt are mixed with methanol and toluene as solvents to form a polymer electrolyte mixture. In some examples, metal oxide particles are added to the electrolyte mixture. The electrolyte mixture is then hand-cast and smoothed between two pieces of MYLAR (a biaxially oriented polyester film available from E.I. duPont deNemours, Wilmington, Del., USA) that are coated with a silicone release material. This forms a smooth layer of the polymer electrolyte, which is then dried to remove solvent, resulting in a polymer electrolyte sheet having a thickness of about 12 mils (about 0.3 mm). After removing the MYLAR film, the dry sheet is cut into square sheets having side dimensions of about 1½ inches (about 3.8 cm). The square sheets are then placed onto clean room paper and are pressed to a thickness of from about 6 mils to about 8 mils (about 150 μm to about 200 μm).

Thereafter, a thick-film paste is screen printed onto each of the squares to form an electrode pattern and the screen printed electrode material is dried at room temperature. The electrodes are screen printed in a pattern such that after dicing the working electrodes will be exposed and the counter/reference electrodes will be buried in the polymer electrolyte except for an exposed edge used for termination. The square sheets are then selectively stacked one on top of each other and are then heated at about 40° C. to release the polymer electrolyte from the clean room paper. The polymer flows slightly and forms a monolithic structure. The structure is then placed in an isostatic laminator and is pressed at a pressure of about 2000 psi and a temperature of about 60° C. to remove air pockets and further consolidate the structure. Thereafter, the laminated structure is diced to form individual multilaminate structures. A silver thick-film paste is applied to the edges having exposed electrode microbands to serve as the termination portion of the electrodes.

Example 1

A multilaminate sensor is produced that can be used for the detection of $H_2S$. To fabricate the sensor, a polymer electrolyte is formed that includes 15 wt. % $LiClO_4$ in poly(ethylene oxide) having a molecular weight of 5M. The formulation includes 50 wt. % methanol, 25 wt. % toluene, 1 wt. % plasticizer (SANTICIZER 160, available from the Ferro Corporation, Walton Hills, Ohio, USA), 1 wt. % dispersant (DISPERBYK 103, available from BYK Chemie, Wallingford, Conn., USA) 3 wt. % $LiClO_4$ and 20 wt. % poly (ethylene oxide). The working electrode microbands are formed from a thick-film gold paste and the counter/reference electrode microbands are formed from a thick-film platinum paste. Each paste also includes a small amount of poly(ethylene oxide).

The layers are stacked and laminated as described above such that the sensor includes a working electrode with 7 microbands and a counter/reference electrode with 6 microbands, each of the counter/reference electrode microbands being disposed between adjacent working electrode microbands.

The sensor is tested using a 0 mV bias between the electrodes. Specifically, the sensor is exposed to air for a period of time, followed by exposure to a test gas. Test gases are blended from certified cylinders of the target analyte using computer controlled mass flow controllers. After gas exposure, the sensors are again exposed to air. The current response is recorded. The sensors are exposed to 10 ppm of $H_2S$, followed by a linearity study where the sensors are exposed to steps of 5, 10, 20 and 50 ppm of $H_2S$ with air exposure between each step. A diffusion restrictor is used during testing of the sensors.

Figure 11:
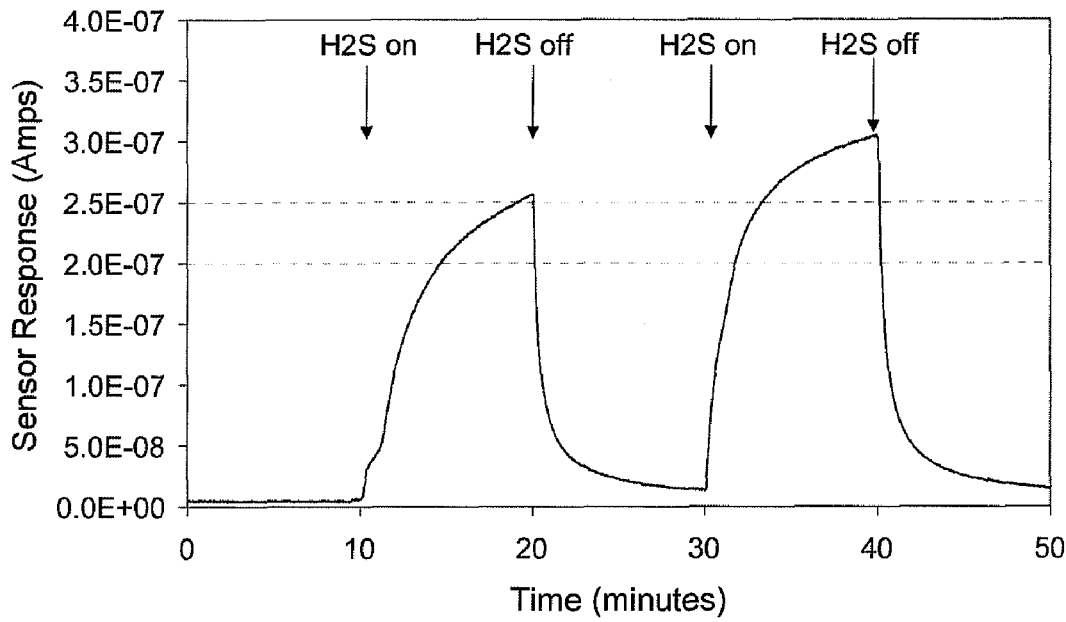
FIG. 11 illustrates the response time of an electrochemical sensor according to an embodiment of the present invention.
Figure 12:
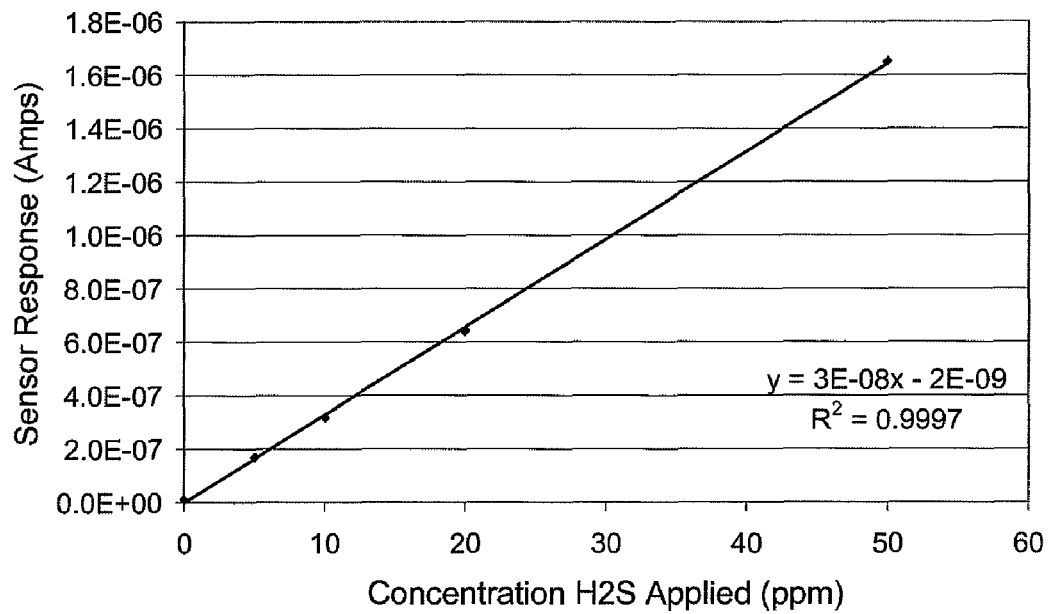
FIG. 12 illustrates the response linearity of an electrochemical sensor according to an embodiment of the present invention.

The test results are illustrated in FIG. 11 and FIG. 12. FIG. 11 illustrates the sensor response time to an atmosphere comprising 10 ppm $H_2S$. FIG. 12 illustrates that the sensor has good linear response at concentrations of $H_2S$ up to 50 ppm.

Example 2

A sensor is fabricated in a substantially identical manner as in Example 1, except that the polymer electrolyte includes 12 wt. % $Al_2O_3$ having an average particle size in the range of about 0.9 μm to 2.2 μm. The sensor is tested in a manner similar to Example 1, however in Example 2 the sensor is exposed to an atmosphere containing 5 ppm $H_2S$.

Figure 13:
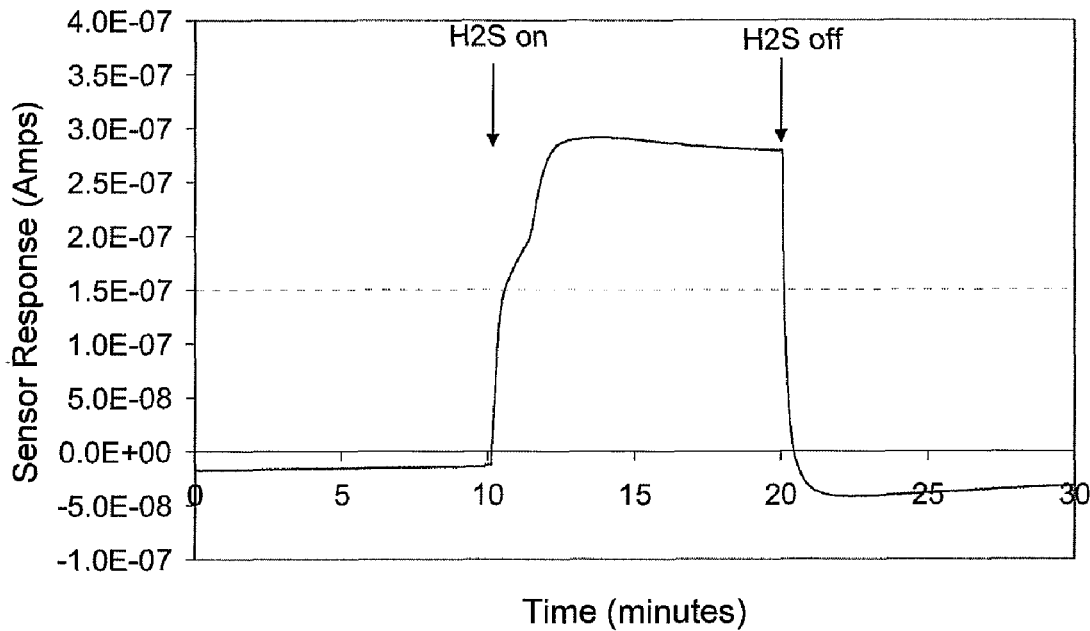
FIG. 13 illustrates the response time of an electrochemical sensor according to an embodiment of the present invention.
Figure 14:
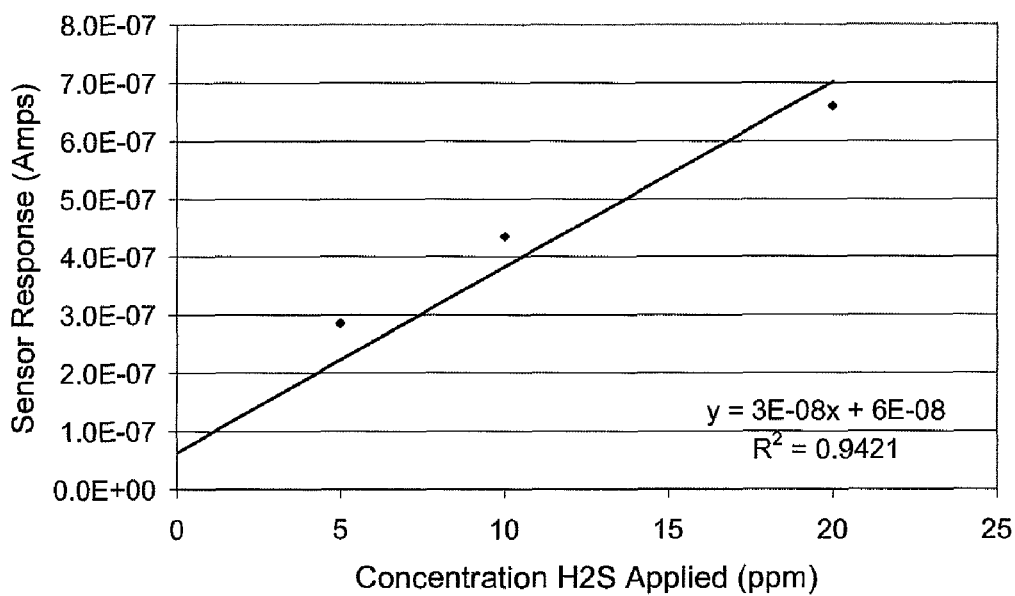
FIG. 14 illustrates the response linearity of an electrochemical sensor according to an embodiment of the present invention.

As can be seen from FIG. 13 and FIG. 14, the sensor has a faster response time as compared to Example 1 and had a total response that was equal to or higher than Example 1, despite the presence of 50 percent less $H_2S$. However, the average linearity of the sensor response (FIG. 14) decreased slightly as compared to Example 1.

Example 3

A multilaminate sensor is fabricated that can be used for the detection of $H_2S$. To fabricate the sensor, a polymer electrolyte is formed that includes 13.6 wt. % $LiBF_4$ in poly (ethylene oxide) having a molecular weight of 5M. The polymer electrolyte formulation is substantially identical to that in Example 1, with $LiBF_4$ being substituted for the $LiClO_4$. The working electrode microbands are formed from a thick-film gold paste and the counter/reference electrode microbands are formed from a thick-film platinum paste. Each paste also includes a small amount of poly(ethylene oxide).

The layers are stacked and laminated as described above such that the sensor includes a working electrode with 5 microbands and a counter/reference electrode with 4 microbands, each of the counter/reference electrode microbands being disposed between adjacent working electrode microbands.

The sensor is tested using a 0 mV bias between the electrodes. Specifically, the sensor is exposed to air for a period of time, followed by exposure to a test gas. The test gas is blended from certified cylinders of the target analyte using computer controlled mass flow controllers. After exposure to the test gas, the sensors are again exposed to air. The current response is recorded. The sensors are exposed to 10 ppm $H_2S$, followed by a linearity study where the sensors are exposed to steps of 2.5, 5, 10, and 20 ppm $H_2S$ with exposure to air between each step. A diffusion restrictor is used during testing of the sensors.

Figure 15:
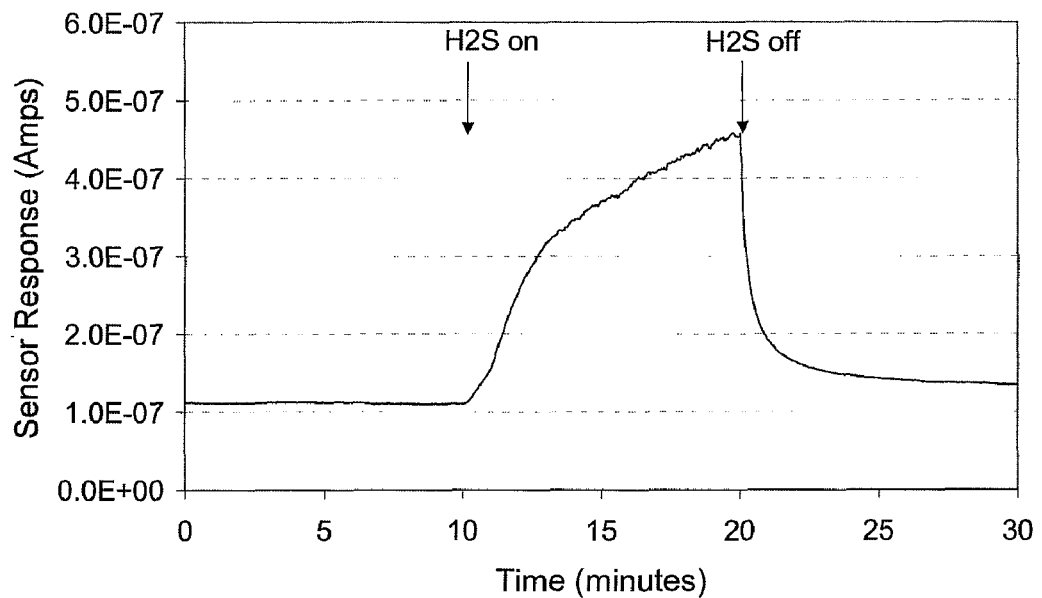
FIG. 15 illustrates the response time of an electrochemical sensor according to an embodiment of the present invention.
Figure 16:
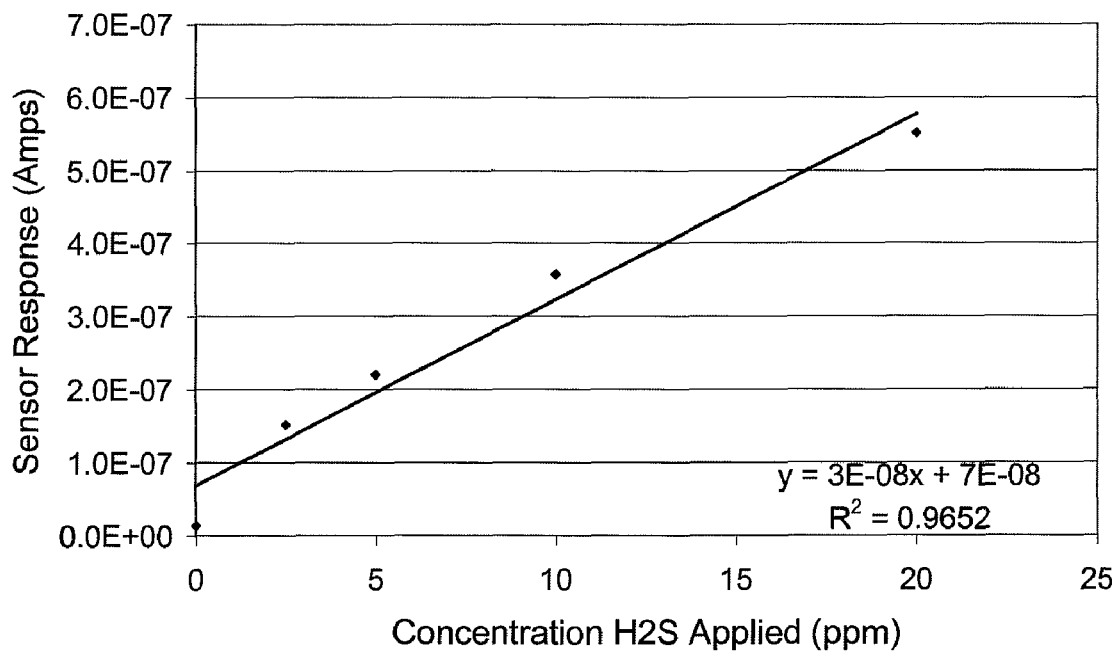
FIG. 16 illustrates the response linearity of an electrochemical sensor according to an embodiment of the present invention.

The test results are illustrated in FIG. 15 and FIG. 16. FIG. 15 illustrates the sensor response time to an atmosphere comprising 10 ppm $H_2S$ and FIG. 16 illustrates the average linearity of the sensor response.

Example 4

A multilaminate sensor is fabricated that can be used for the detection of $H_2S$. To fabricate the sensor, a polymer electrolyte is formed that includes 13.6 wt. % $LiBF_4$ in poly (ethylene oxide) having a molecular weight of 5M. The polymer electrolyte formulation is the same as the formulation in Example 3. The working electrode microbands are formed from a thick-film gold paste and the counter/reference electrode microbands are formed from a thick-film silver/silver chloride (Ag/AgCl) paste. A small amount of polymer is included in the gold paste composition.

The layers are stacked and laminated as described above such that the sensor includes a working electrode with 5 gold microbands and a counter/reference electrode with 4 silver/silver chloride microbands, each of the counter/reference electrode microbands being disposed between adjacent working electrode microbands.

The sensor is tested using a 500 mV bias between the electrodes. Specifically, the sensor is exposed to air for a period of time, followed by exposure to a test gas. The test gas is blended from certified cylinders of the target analyte using computer controlled mass flow controllers. After exposure to the test gas, the sensors are again exposed to air. The current response is recorded. The sensors are exposed to 10 ppm $H_2S$, followed by a linearity study where the sensors are exposed to steps of 1, 2, 5, and 10 ppm $H_2S$ with exposure to air between each step. A diffusion restrictor is used during testing of the sensors.

Figure 17:
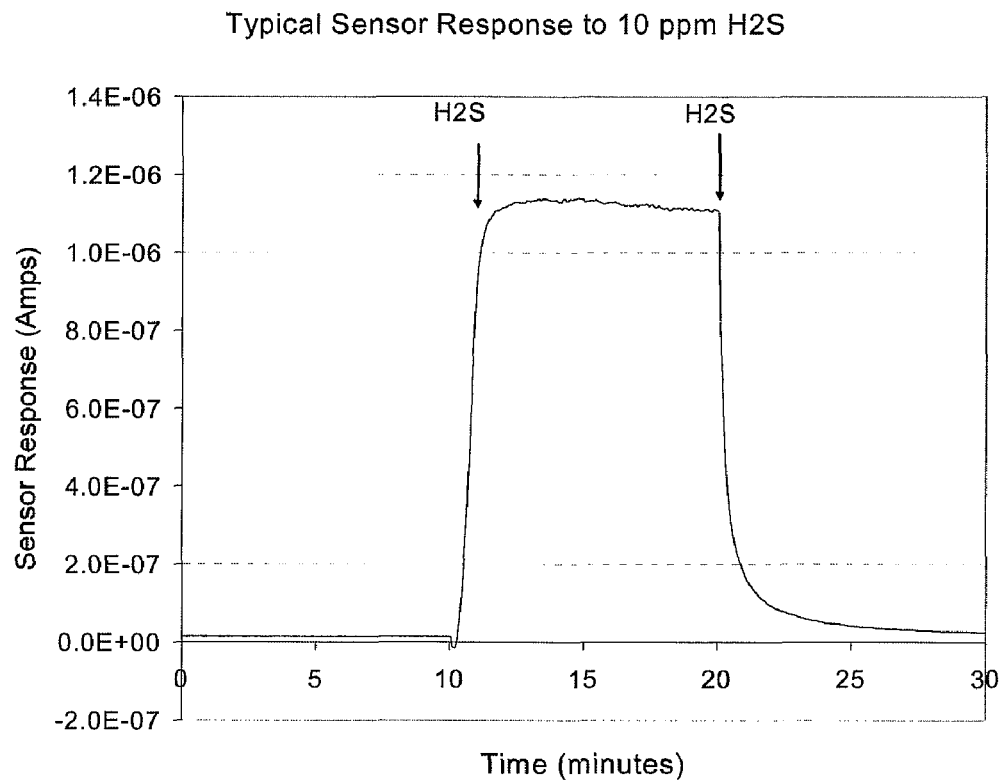
FIG. 17 illustrates the response time of an electrochemical sensor according to an embodiment of the present invention.
Figure 18:
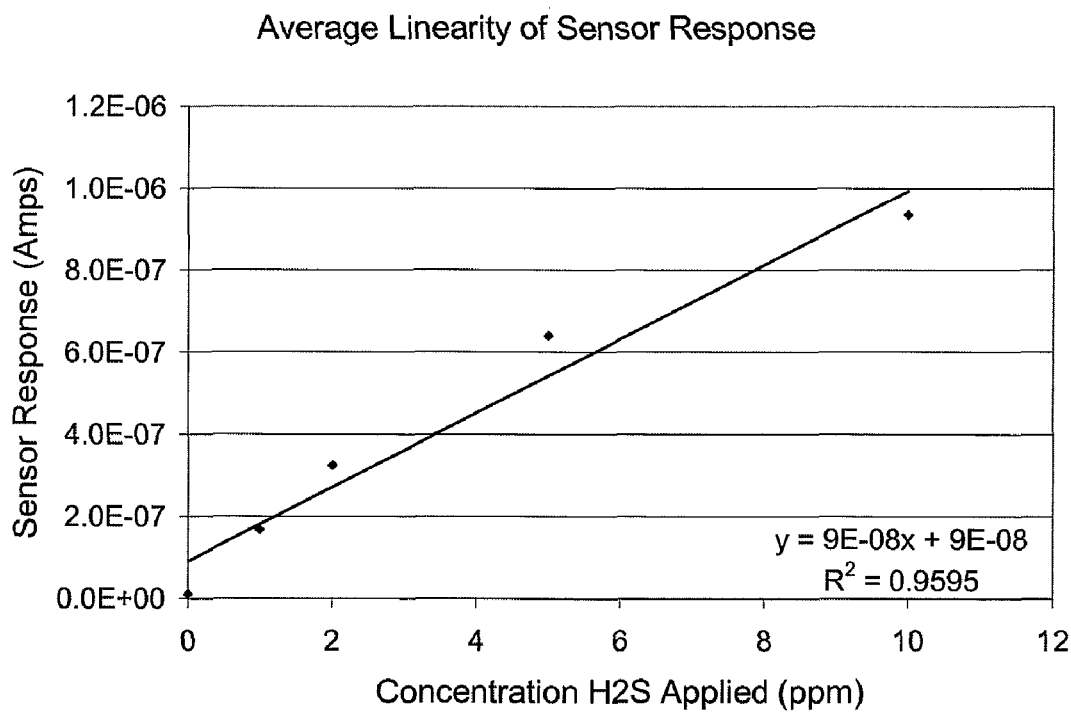
FIG. 18 illustrates the response linearity of an electrochemical sensor according to an embodiment of the present invention.

The test results are illustrated in FIG. 17 and FIG. 18. FIG. 17 illustrates the sensor response time to an atmosphere comprising 10 ppm $H_2S$ and FIG. 18 illustrates the average linearity of the sensor response.

Example 5

A multilaminate sensor is fabricated that can be used for the detection of carbon monoxide (CO) or ethanol ($C_2H_6O$). To fabricate the sensor, a polymer electrolyte is formed that includes 15 wt. % $LiClO_4$ in poly (ethylene oxide) having a molecular weight of 5 M. The working electrode microbands are formed from a thick film platinum paste and a counter/reference electrode microbands are also formed from a thick-film platinum paste.

The layers are stacked and laminated as described above such that the sensor includes five working electrodes and four counter/reference electrodes, each of the counter/reference electrode microbands being disposed between adjacent working electrode microbands.

Figure 19:
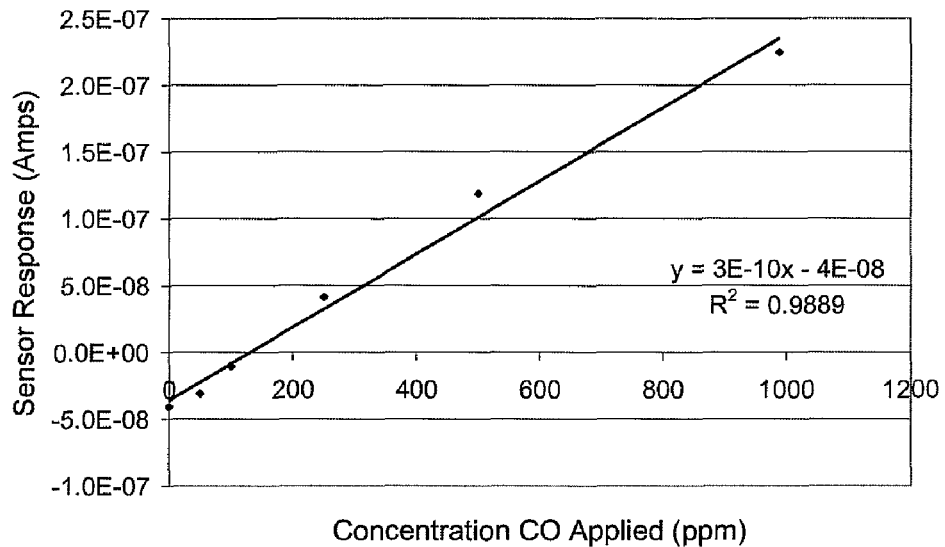
FIG. 19 illustrates the response time of an electrochemical sensor according to an embodiment of the present invention.
Figure 20:
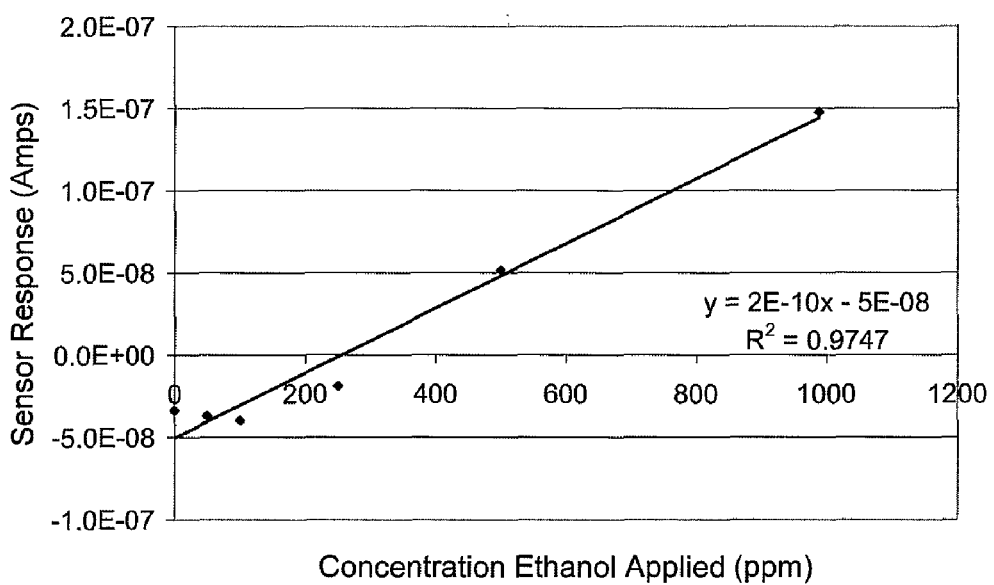
FIG. 20 illustrates the response linearity of an electrochemical sensor according to an embodiment of the present invention.

The results for CO detection are illustrated in FIG. 19 and the results for detection of ethanol are illustrated in FIG. 20.

While various embodiments of the present invention have been described in detail, it is apparent that modifications and adaptations of those embodiments will occur to those skilled in the art. However, is to be expressly understood that such modifications and adaptations are within the spirit and scope of the present invention.

What is claimed is:

1. An electrochemical sensor for detecting a chemical species in an environment, comprising:
   a) a solid polymer electrolyte comprising a solid polymer matrix and a salt dispersed within said solid polymer matrix;
   b) a working electrode comprising a plurality of planar spaced-apart microbands disposed within and separated by said solid polymer electrolyte where the working electrode is adapted to catalyze the oxidation or reduction reaction of the chemical species and at least a portion of the interface between the working electrode microbands and the solid polymer electrolyte is in direct contact with the environment that is being sampled, wherein at least one outer edge of the working electrode microbands extends to the exterior surface of the sensor; and
   c) a counter electrode contacting said solid polymer electrolyte, wherein said working electrode is separated from said counter electrode by said solid polymer electrolyte.

2. An electrochemical sensor as recited in claim 1, wherein at least two outer edges of the working electrode microbands extend to the exterior surface of the sensor.

3. An electrochemical sensor as recited in claim 1, wherein said solid polymer matrix is selected from the group consisting of poly(oxides), poly(vinyl ethers), polyvinylpyrrolidone, poly(acrylics), poly(methacrylics) and polyvinyl alcohol.

4. An electrochemical sensor as recited in claim 1, wherein said solid polymer matrix comprises a poly(oxide).

5. An electrochemical sensor as recited in claim 1, wherein said solid polymer matrix comprises poly(ethylene oxide).

6. An electrochemical sensor as recited in claim 1, wherein said solid polymer matrix is amorphous.

7. An electrochemical sensor as recited in claim 1, wherein said solid polymer matrix has a molecular weight of at least about 100,000 and not greater than about 10,000,000.

8. An electrochemical sensor as recited in claim 1, wherein said salt is a monovalent cation salt.

9. An electrochemical sensor as recited in claim 1, wherein said salt is an inorganic salt selected from the group consisting of a lithium salt, a sodium salt, an ammonium salt and a magnesium salt.

10. An electrochemical sensor as recited in claim 1, wherein said salt is selected from the group consisting of lithium perchlorate, lithium tetrafluorborate, lithium chloride, sodium chlorate, sodium perchlorate, sodium tetrafluroborate, ammonium tetrafluorborate and ammonium perchlorate.

11. An electrochemical sensor as recited in claim 1, wherein said salt comprises lithium perchlorate.

12. An electrochemical sensor as recited in claim 1, wherein said solid polymer electrolyte comprises at least about 10 wt. % and not greater than about 15 wt. % of said salt.

13. An electrochemical sensor as recited in claim 1, wherein said working electrode comprises a material selected from the group consisting of gold, platinum, silver, palladium, ruthenium, iridium, carbon and mixtures thereof.

14. An electrochemical sensor as recited in claim 1, wherein said working electrode comprises a noble metal.

15. An electrochemical sensor as recited in claim 1, wherein said working electrode comprises gold.

16. An electrochemical sensor as recited in claim 1, wherein said working electrode comprises platinum.

17. An electrochemical sensor as recited in claim 1, wherein said working electrode comprises a material that is different than said counter electrode.

18. An electrochemical sensor as recited in claim 1, wherein said counter electrode comprises platinum.

19. An electrochemical sensor as recited in claim 1, wherein said counter electrode is also a reference electrode.

20. An electrochemical sensor as recited in claim 1, further comprising a reference electrode that is distinct from said counter electrode.

21. An electrochemical sensor as recited in claim 1, wherein said solid polymer electrolyte comprises at least about 2 wt. % of said salt.

22. An electrochemical sensor as recited in claim 21, wherein said solid polymer electrolyte comprises not greater than about 25 wt. % of said salt.

23. An electrochemical sensor as recited in claim 1, wherein said solid polymer electrolyte further comprises inorganic particulates dispersed within said solid polymer matrix.

24. An electrochemical sensor as recited in claim 23, wherein said solid polymer electrolyte comprises at least about 3 wt. % and not greater than about 15 wt. % of said inorganic particulates.

25. An electrochemical sensor as recited in claim 23, wherein said inorganic particulates have an average particle size of not greater than about 1 μm.

26. An electrochemical sensor as recited in claim 23, wherein said inorganic particles have an average particle size of at least about 5 nanometers and not greater than about 500 nanometers.

27. An electrochemical sensor as recited in claim 23, wherein said inorganic particulates comprise metal oxide particulates.

28. An electrochemical sensor as recited in claim 27, wherein said inorganic particulates are selected from the group consisting of aluminum oxide, silica and titania.

29. An electrochemical sensor as recited in claim 1, wherein said counter electrode comprises a plurality of spaced-apart microbands that are disposed within said solid polymer electrolyte, the counter electrode microbands being disposed between said working electrode microbands and defining layers of solid polymer electrolyte therebetween.

30. An electrochemical sensor as recited in claim 29, wherein said electrochemical sensor comprises at least 5 working electrode microbands and at least 4 counter electrode microbands.

31. An electrochemical sensor as recited in claim 29, wherein said layers of solid polymer electrolyte have an average thickness of at least about 25 μm and not greater than about 2.5 mm.

32. An electrochemical sensor as recited in claim 31, wherein said polymer electrolyte layers have an average thickness of not greater than about 1 mm.

33. An electrochemical sensor for detecting a chemical species in an environment, comprising:
   a) a solid polymer electrolyte comprising a solid polymer matrix and a salt dispersed within said solid polymer matrix;
   b) a working electrode comprising a plurality of spaced-apart microbands that are disposed within said solid polymer electrolyte and comprising a termination portion on an outer surface of the sensor, wherein at least one outer edge of the working electrode microbands terminates on an outer edge surface of the sensor to provide a three-phase interface between the solid polymer electrolyte, the working electrode and the environment; and
   c) a counter electrode contacting said solid polymer electrolyte, wherein said working electrode is separated from said counter electrode by said solid polymer electrolyte.

34. An electrochemical sensor as recited in claim 33, wherein said solid polymer matrix is selected from the group consisting of poly(oxides), poly(vinyl ethers), polyvinylpyrrolidone, poly(acrylics), poly(methacrylics) and polyvinyl alcohol.

35. An electrochemical sensor as recited in claim 33, wherein said solid polymer matrix comprises a poly(oxide).

36. An electrochemical sensor as recited in claim 33, wherein said solid polymer matrix comprises poly(ethylene oxide).

37. An electrochemical sensor as recited in claim 33, wherein said salt is a monovalent cation salt.

38. An electrochemical sensor as recited in claim 33, wherein said salt is an inorganic salt selected from the group consisting of a lithium salt, a sodium salt, an ammonium salt and a magnesium salt.

39. An electrochemical sensor as recited in claim 33, wherein said salt is selected from the group consisting of lithium perchlorate, lithium tetrafluoborate, lithium chloride, sodium chlorate, sodium perchlorate, sodium tetrafluorborate, ammonium tetrafluorborate and ammonium perchlorate.

40. An electrochemical sensor as recited in claim 33, wherein said salt comprises lithium perchlorate.

41. An electrochemical sensor as recited in claim 33, wherein said solid polymer electrolyte comprises at least about 2 wt. % of said salt and not greater than about 25 wt. % of said salt.

42. An electrochemical sensor as recited in claim 33, wherein said working electrode comprises a material selected from the group consisting of gold, platinum, silver, palladium, ruthenium, iridium, carbon and mixtures thereof.

43. An electrochemical sensor as recited in claim 33, wherein said working electrode comprises gold.

44. An electrochemical sensor as recited in claim 33, wherein said working electrode comprises platinum.

45. An electrochemical sensor as recited in claim 33, wherein said working electrode comprises a material that is different than said counter electrode.

46. An electrochemical sensor as recited in claim 33, wherein a portion of the interface between the working electrode and the solid polymer electrolyte is in contact with the environment surrounding the sensor.

47. An electrochemical sensor as recited in claim 33, wherein at least two outer edges of the working electrode microbands terminate on an outer edge surface of the sensor.

48. An electrochemical sensor as recited in claim 33, wherein said counter electrode comprises a plurality of spaced-apart microbands that are disposed within said solid polymer electrolyte, the counter electrode microbands being disposed between said working electrode microbands and defining layers of solid polymer electrolyte therebetween.

49. An electrochemical sensor as recited in claim 48, wherein said layers of solid polymer electrolyte have an average thickness of at least about 25 μm and not greater than about 2.5 μm.

50. An electrochemical sensor as recited in claim 33, wherein said solid polymer electrolyte further comprises inorganic particulates dispersed within said solid polymer matrix.

51. An electrochemical sensor as recited in claim 50, wherein said solid polymer electrolyte comprises at least about 3 wt. % and not greater than about 15 wt. % of said inorganic particulates.

52. An electrochemical sensor as recited in claim 50, wherein said inorganic particulates comprise metal oxide particulates.

53. An electrochemical sensor for detecting a chemical species in an environment, comprising:
   a) a solid polymer electrolyte comprising a solid polymer matrix selected from the group consisting of poly(oxides), poly(vinyl ethers), polyvinylpyrrolidone, poly(acrylics), poly(methacrylics) and polyvinyl alcohol and a salt dispersed within said solid polymer matrix;
   b) a working electrode comprising a plurality of spaced-apart microbands that are disposed within said solid polymer electrolyte, wherein said spaced-apart microbands are exposed to the environment along at least one edge of the sensor; and
   c) a counter electrode, wherein said working electrode is separated from said counter electrode by said solid polymer electrolyte and wherein said counter electrode comprises a plurality of spaced-apart microbands that are disposed within said solid polymer electrolyte, the counter electrode microbands being disposed between said working electrode microbands and defining layers of solid polymer electrolyte therebetween.

54. An electrochemical sensor as recited in claim 53, wherein said spaced-apart microbands are exposed to the environment along at least two edges of the sensor.

* * * * *

UNITED STATES PATENT AND TRADEMARK OFFICE
CERTIFICATE OF CORRECTION

| | | |
|---|---|---|
| PATENT NO. | : 7,918,977 B2 | |
| APPLICATION NO. | : 11/533729 | |
| DATED | : April 5, 2011 | |
| INVENTOR(S) | : Deininger et al. | |

It is certified that error appears in the above-identified patent and that said Letters Patent is hereby corrected as shown below:

IN THE CLAIMS:

Claim 10, col. 18, line 14, delete "tetrafluorborate" and insert --tetrafluoroborate--.
Claim 10, col. 18, line 15-16, delete "tetrafluroborate" and insert --tetrafluoroborate--.
Claim 10, col. 18, line 16, delete "tetrafluorborate" and insert --tetrafluoroborate--.
Claim 39, col. 19, line 57, delete "tetrafluorborate" and insert --tetrafluoroborate--.
Claim 39, col. 19, line 58-59, delete "tetrafluorborate" and insert --tetrafluoroborate--.
Claim 39, col. 19, line 59, delete "tetrafluorborate" and insert --tetrafluoroborate--.

Signed and Sealed this
Seventeenth Day of May, 2011

David J. Kappos
*Director of the United States Patent and Trademark Office*